United States Patent
Seeman et al.

(10) Patent No.: US 8,841,428 B2
(45) Date of Patent: Sep. 23, 2014

(54) POLYNUCLEOTIDE NANOMECHANICAL DEVICE THAT ACTS AS AN ARTIFICIAL RIBOSOME AND TRANSLATES DNA SIGNALS INTO POLYMER ASSEMBLY INSTRUCTIONS

(75) Inventors: Nadrian C. Seeman, New York, NY (US); Shiping Liao, New York, NY (US); James Canary, New York, NY (US); Hong Zhong, Brooklyn, NY (US)

(73) Assignee: New York University, New York, NY (US)

( * ) Notice: Subject to any disclaimer, the term of this patent is extended or adjusted under 35 U.S.C. 154(b) by 1847 days.

(21) Appl. No.: 11/192,401

(22) Filed: Jul. 29, 2005

(65) Prior Publication Data

US 2006/0035255 A1    Feb. 16, 2006

Related U.S. Application Data

(60) Provisional application No. 60/592,402, filed on Aug. 2, 2004.

(51) Int. Cl.
| | | |
|---|---|---|
| *C07H 21/00* | (2006.01) | |
| *C07H 19/067* | (2006.01) | |
| *C12P 19/34* | (2006.01) | |
| *B82Y 5/00* | (2011.01) | |
| *B82Y 15/00* | (2011.01) | |
| *C12N 15/10* | (2006.01) | |
| *C12P 21/02* | (2006.01) | |

(52) U.S. Cl.
CPC .  *C12P 19/34* (2013.01); *B82Y 5/00* (2013.01); *B82Y 15/00* (2013.01); *C12N 15/10* (2013.01); *C12N 15/1031* (2013.01); *C12P 21/02* (2013.01)
USPC .......................................... 536/23.1; 536/22.1

(58) Field of Classification Search
None
See application file for complete search history.

(56) References Cited

U.S. PATENT DOCUMENTS 3,538,193 A  *  11/1970  Meredith ...................... 528/486
7,479,548 B1     1/2009  Canary et al.
7,943,751 B2     5/2011  Canary et al.

FOREIGN PATENT DOCUMENTS

WO    2005/001035 A2    1/2005

OTHER PUBLICATIONS

Landweber et al. DNA2DNA computations: A potential "killer app"? Lecture Notes in Computer Science. vol. 1256, 1997, pp. 56-64.*
Zhu et al. Nylon/DNA: Single stranded DNA with a covalently stitched nylon lining. Journal of the American Chemical Society, Aug. 5, 2003, vol. 125, pp. 10178-10179.*
Yan et al. A robust DNA mechanical device controlled by hybridization topology. Nature. Jan. 2002, vol. 415, pp. 62-65.*
Jonoska et al. Transducers with programmable input by DNA self-assembly. Lecture Notes in Computer Science, vol. 2950, Feb. 19, 2004, pp. 219-240.*
Clarke L. Journal of the American Chemical Society, 1909, vol. 31, pp. 585-590.*
Hudson RDA. Ferrocene polymers: current architectures, syntheses and utility. Journal of Organometallic Chemistry. 2001, vols. 637-639, pp. 47-69.*
Definition of "dimer." Webster's Third New International Dictionary. 1993, Merriam-Webster Incorporated, 1 page printout.*
Curriculum Vitae of James Canary, ten pages, obtained online from NYU website on Sep. 3, 2013.*
Mathews et al. Biochemistry. New York: The Benjamin/Cummings Publishing Company, Inc., 1990, pp. 142-143, 962-964, and 984.*
Liu et al.,Coupling Across a DNA Helical Turn Yields a Hybrid DNA/Organic Catenane Doubly Tailed with Functional Termini, J. Am. Chem. Soc. 130:10882-10883 (2008).
Liu et al., Templated synthesis of nylon nucleic acids and characterization by nuclease digestion, Chem. Sci. 3:1930-1937 (2012).
Supporting Information (pp. S1-S14) for Zhu et al., Nylon/DNA: Single-Stranded DNA with a Covalently Stitched Nylon Lining, J. Am. Chem. Soc. 125:10178-10179 (2003), available at http://pubs.acs.org.

* cited by examiner

*Primary Examiner* — Russell S Negin
(74) *Attorney, Agent, or Firm* — Browdy and Neimark, PLLC

(57) ABSTRACT

A polynucleic acid nanomechanical device with a linear array of alternating PX-JX$_2$ devices and nucleic acid multi-crossover motifs that facilitate the assembly of a nucleic acid strand and functions as an artificial ribosome by translating a nucleic acid signal into an unrelated nucleic acid sequence.

2 Claims, 11 Drawing Sheets

PRIOR ART

FIG. 8A
FIG. 8B
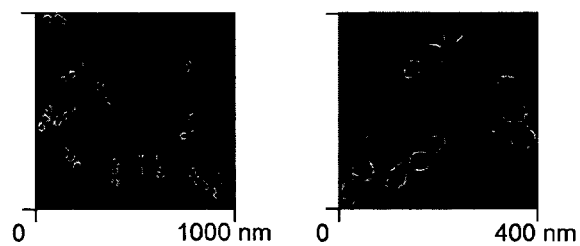
FIG. 8C        FIG. 8D
FIG. 9

POLYNUCLEOTIDE NANOMECHANICAL DEVICE THAT ACTS AS AN ARTIFICIAL RIBOSOME AND TRANSLATES DNA SIGNALS INTO POLYMER ASSEMBLY INSTRUCTIONS

CROSS-REFERENCE TO RELATED APPLICATIONS

The present application claims the benefit of priority under 35 U.S.C. §119(e) from provisional U.S. application no. 60/592,402, filed Aug. 2, 2004, the entire content of which is herein incorporated by reference.

GOVERNMENT LICENSE RIGHTS

The experiments reported in this application were supported in part by: the National Institute of General Medical Sciences, grant no. GM-29554; the Office of Naval Research, grant no. N00014-98-1-0093; the National Science Foundation, grant nos. DMI-0210844, EIA-0086015, DMR-01138790 and CTS-0103002; and DARPA/AFSOR, grant no. F30602-01-2-0561. The U.S. Government has a paid-up license in this invention and the right in limited circumstances to require the patent owner to license others on reasonable terms as provided for by the terms of the above grants.

BACKGROUND OF THE INVENTION

1. Field of the Invention

The present invention relates to molecular scale mechanical devices.

2. Description of the Related Art

The PX-JX$_2$ device is a sequence-dependent DNA machine whose state is controlled by hybridization topology (Yan et al., 2002). It can assume two structural states that differ from each other by a half-turn rotation of one end of the molecule 180° relative to the other end (FIG. 1). Two different pairs of 'set strands' can bind to the framework of the device, thereby establishing which structural state it adopts. The set strands contain short unpaired segments ('toeholds') at one of their ends to facilitate their removal by 'unset' strands that bind to the toeholds and then remove the set strands by branch migration (Yurke et al., 2000).

A system with plural PX-JX$_2$ devices is presented in Yan et al. (2002) and in U.S. patent publication 2003-0219790. This system contains half-hexagon markers connected into oligomeric arrays by linkage through extensions that include PX-JX$_2$ devices. If the PX-JX$_2$ devices are all in the PX state, the half-hexagons have a cis arrangement, where they all point in the same direction. However, when the devices are all in the JX$_2$ state, the half-hexagons form a zigzag trans structure. In addition to the PX-JX$_2$ device, numerous variants of sequence-dependent control, pioneered in DNA tweezers by Yurke et al. have been reported; these include a DNA actuator (Simmel et al., 2001), a 3-state device (Simmel et al., 2002), and a DNA bipedal walking machine (Sherman et al., 2004).

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such a statement.

SUMMARY OF THE INVENTION

The present invention provides a polynucleic acid nanomechanical device that functions as an artificial ribosome by translating a nucleic acid signal into an unrelated sequence. This polynucleic acid nanomechanical device is based on a linear array of alternating PX-JX$_2$ devices and nucleic acid multi-crossover motifs having a central dyad axis. The nucleic acid multi-crossover motifs have wings which are symmetrical to each other along its central dyad axis. Each symmetrical wing contains a double helical domain parallel to the central dyad axis, which-double helical domain has two sequence specific cohesive ends capable of cohesion with complementary cohesive ends. By independently setting the state of each PX-JX$_2$ device to either the PX or JX$_2$ topoisomeric state using, as nucleic acid signals, different sequence specific set strands, the polynucleic acid nanomechanical device of the present invention can assemble a nucleic acid strand or a polymer attached thereto from a collection of building blocks of nucleic acid multi-crossover molecules by cohesion between the sequence specific cohesive ends of the double helical domain of a symmetrical wing parallel to the central dyad axis and the sequence specific cohesive ends of the collection of nucleic acid multi-crossover molecules.

The present invention also provides a polymer capable of being formed by the polynucleic acid nanomechanical device of the present invention and a process for producing such a polymer using the polynucleic acid nanomechanical device of the present invention to assemble an intermediate polymer molecule from which the polymer is produced by desulfurization reaction.

BRIEF DESCRIPTION OF THE DRAWINGS

FIG. 8A-8D show the characterization and purification of a plural PX-JX$_2$ polynucleic acid nanomechanical device of the present invention. The intact structure of the double diamond units is shown on a 3.5% non-denaturing gel of the complex, composed of all 22 strands (FIGS. 8A and 8B). LM indicates linear markers. Each of the strands (numbered as in FIG. 3) is labeled separately with radioactive phosphate. The number above each lane shows the labeled strand. In each case, the strand is incorporated cleanly into the complex, with no doubling and no breakdown products evident. Atomic force microscopy images of the purified device are presented in FIGS. 8C and 8D. The images were prepared as described previously (Yan et al., 2002 and U.S. patent publication 2003-0219790). The DX molecules were omitted for clarity in the image. FIG. 8C is a large field image and FIG. 8D is a zoom image. Note that the single and double double-diamond nature of the complex is evident from the small-large-large nature of the sample molecules. It is clear that the purification protocol used is quite successful at eliminating failure products from the sample.

FIG. 9 is a 6% denaturing gel autoradiogram illustrating the products of the ligation. The first lane contains a 50 nucleotide ladder. Lanes 2-5 contain, respectively, the products of setting the device states to PX-PX, PX-JX$_2$, JX$_2$-PX, and JX$_2$-JX$_2$. The upper strand (FIG. 7) is labeled in each case. The target band is prominent in all lanes, although failure products are evident.

DETAILED DESCRIPTION OF THE INVENTION

The advent of translation was a hallmark development in the evolution of life: It signaled the end of the RNA world, because nucleic acids could code for chemical species whose properties were not derived directly from the transcription of their parent molecules. The present inventors have built a polynucleotide nanomechanical device that performs the same task, and thus functions in a fashion that is logically equivalent to a ribosome. In response to a nucleic acid signal, this device aligns a series of molecules that are then bonded together. A prototype of this system with DNA, so the products are DNA oligonucleotides of a defined sequence, is shown in the Example presented hereinbelow. Thus, in this case, the chemistry of the product is similar to that of the signal molecules, but there is no complementary relationship to the signal sequences. By using DNA molecules to set the states of two DNA PX-JX2 devices (Yan et al., 2001 and 2002; U.S. patent publication 2003-02319790) independently, the present inventors have programmed the synthesis of four different product molecules.

Figure 2:
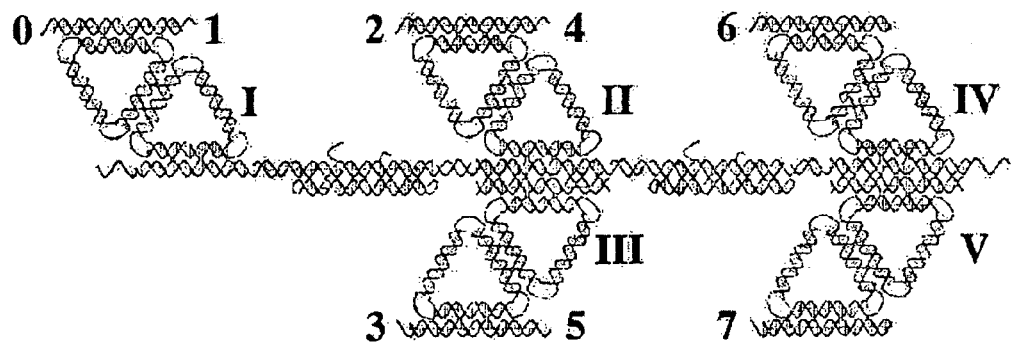
FIG. 2 shows the structure of a preferred embodiment of a plural PX-JX$_2$ device. Five diamond motifs (Yan et al., 2001) are labeled by Roman numerals, and the sticky ends are labeled by Arabic numerals. The diamonds are connected to form double-diamond wings via a PX linkage, to give the wings dyad symmetry (Shen et al., 2004). There is an 'initiator' diamond motif at the left (I), while two double diamond motifs are at the center and right. The initiator diamond and the double diamonds are connected by PX-JX$_2$ devices, so the relative orientations of the sticky ends can be varied.

Two PX-JX2 devices have been incorporated in succession, controlling the relative orientations of a diamond-shaped motif (Yan et al., 2001) and a pair of double-diamond-shaped wings, as shown in FIG. 2. The Arabic numerals in FIG. 2 designate individual cohesive/sticky ends available to bind DNA double crossover (DX) molecules (Fu et al., 1993) that contain a continuous DNA strand extending from one end to the other. This continuous strand ultimately will be a component of the product. The rest of the DX molecule plays a role analogous to that of tRNA in translation: It serves as an adaptor between the strand that it-carries and the device. The set strands of the device contain the signal or 'message' that configures the sticky ends to bind one of a pair of DX molecules in each of the two gaps.

As disclosed in the art, i.e., Yan et al., 2001 and 2002 and U.S. patent publication 2003-02319790, the entire contents of which are incorporated herein by reference, paranemic crossover (PX) DNA is a four-stranded coaxial DNA structure containing a central dyad axis that relates two flanking parallel double helices. The strands are held together exclusively by Watson-Crick base pairing. The key feature of the molecule is that the two adjacent parallel DNA double helices form crossovers at every point possible. Hence, reciprocal crossover points flank the central dyad axis at every major or minor groove separation. This motif has been modeled and characterized in an oligonucleotide system; a minor groove separation of 5 nucleotide pairs and major groove separations of 6, 7, or 8 nucleotide pairs produce stable PX DNA molecules. Every strand undergoes a crossover every helical repeat (11, 12 or 13 nucleotides), but the period of each strand corresponds to two helical repeats (22, 24 or 26 nucleotides).

The robust polynucleic acid nanomechanical device of the present invention is based on a plurality of nucleic acid paranemic crossover (PX) molecule disposed in a linear array of alternating PX-JX$_2$ devices and nucleic acid multi-crossover motifs, where the state of each PX-JX$_2$ device is independently set between the PX molecule and its JX$_2$ topoisomer. As it is impossible to switch directly from the PX molecule to the JX$_2$ topoisomer or vice versa because of severe topological problems, the laboratory of the present inventors has created a variant of the PX molecule, in which one strand in each of the two strand pairs has been broken down into three segments so that the variant PX molecule can be converted directly to its JX$_2$ topoisomer and cycled back again by the sequential addition of different sets of fuel/unset and set strands. Thus, sections of the PX molecule can be removed and replaced with segments lacking two crossovers to form the $JX_2$ topoisomer molecules. The terms "fuel strands" and "unset strands" are used interchangeably.

Figure 1:
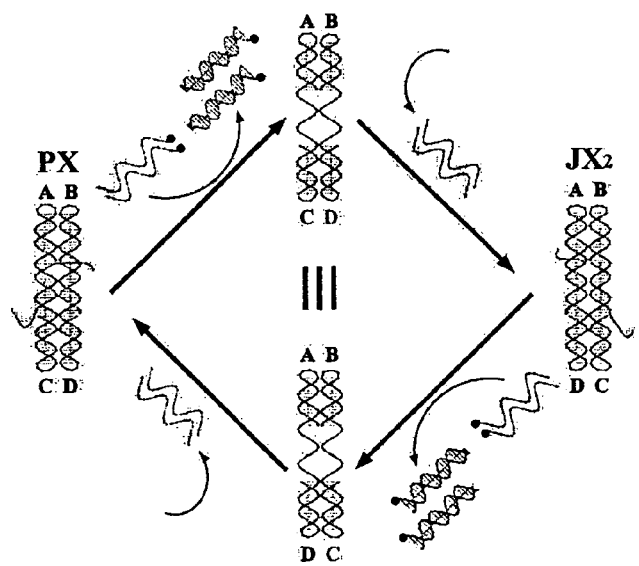
FIG. 1 schematically shows the machine cycle of the PX-JX$_2$ device (Yan et al., 2002; U.S. patent publication 2003-0219790). The PX state of the device is shown at the left, with set strands. These set strands are removed by biotinylated (black dots) unset strands to leave a naked frame (top). Adding different set strands puts the device in the JX$_2$ state. The bottom of the cycle shows restoration of the PX state. The bottom of the cycle shows restoration of the PX state. The two states differ by a half-turn rotation, as highlighted by the letters 'A', 'B', 'C' and 'D' flanking the helices.

As shown in FIG. 1 and in FIGS. 7A and 7B of U.S. patent publication 2003-02319790, the $JX_2$ topoisomer differs from the PX topoisomer in that one pair of ends are rotated 180° relative to the other pair of ends and the $JX_2$ topoisomer has two adjacent sites where two backbones juxtapose without crossing over.

An alternative to the $PX-JX_2$ machine cycle using fuel/unset and set strands shown in FIG. 1 is a $PX-JX_2$ machine cycle using set strands, cover strands and anti-cover strands as disclosed and presented in Example 2 below and in FIG. 11.

Each $PX-JX_2$ device in the polynucleotide nanomechanical device of the present invention is capable of cycling between two topoisomeric states, where a segment, i.e., a middle (internal) segment, of one strand from each strand pair, referred to as being a part of a PX set strand ("sets" the state of the device to be in the PX conformation), is broken from the rest of the strand. The nucleic acid paranemic crossover molecule with PX set strands is converted to its $JX_2$ topoisomer by the addition and incubation with fuel strands (unset) or PX cover strands complementary to the PX set strands to strip the PX set strands from the PX topoisomer, producing an unstructured intermediate, followed by addition and incubation with $JX_2$ set strands or $JX_2$ anti-cover strands to convert the intermediate to the $JX_2$ topoisomer. If the set strands or anti-cover strands added are not $JX_2$ set strands or anti-cover strands but rather PX set strands or anti-cover strands, then the unstructured intermediate can be returned to the PX topoisomeric state instead of being converted to the $JX_2$ topoisomeric state. To cycle back to the PX topoisomeric state, the $JX_2$ topoisomer is converted by addition and incubation with fuel strands or cover strands complementary to the $JX_2$ set strands to strip the $JX_2$ set strands from the $JX_2$ topoisomer, producing an unstructured intermediate, followed by addition and incubation with PX set strands or PX anti-cover strands to convert the intermediate to the PX topoisomer. This four process/step cycle thus leads to two robust end points, the PX state and the $JX_2$ state.

In one preferred embodiment, the PX and $JX_2$ set strands have single stranded unpaired extensions at one end thereof so that such extensions can initiate branch migration that leads to removal of the strand from the branched motif. This is because the set strands are paired with their complementary fuel strands along their entire length. Thus, a complement to the entire length of the set stand (termed a "fuel" or "unset" strand) will pair with it in preference to the partially paired set strand in the PX or $JX_2$ states.

In another preferred embodiment, the PX and $JX_2$ set strands are formed by using either single stranded PX or $JX_2$ cover strands to anneal to control strands having a PX setting portion complementary to PX cover strands and a $JX_2$ setting portion complementary to $JX_2$ cover strands. When only PX cover strands are annealed to the control strands, $JX_2$ set strands are formed because the PX setting portion is covered up by the PX cover strands, allowing the single stranded $JX_2$ setting portion to set the $PX-JX_2$ device to the $JX_2$ state. Conversely, when only $JX_2$ cover strands are annealed to the control strands, PX set strands are formed because the $JX_2$ setting portion is covered up by the $JX_2$ cover strands, thereby allowing the single stranded PX setting portion to set the $PX-JX_2$ device to the PX state. PX and $JX_2$ cover strands are removed from the control strands with PX and $JX_2$ anti-cover strands, respectively. The $PX-JX_2$ device is only a naked frame when the control strands are covered up with both PX and $JX_2$ cover strands. By stripping a cover strand with its cognate anti-cover strand, the fully covered control strand is converted to set strands for setting the state of the $PX-JX_2$ device. For instance, stripping PX cover strands from the control strands with PX anti-cover strands forms PX set strands if the $JX_2$ setting portion on the control strands is already covered up with $JX_2$ cover strands.

Furthermore, it is preferred that one end of the fuel strands or anti-cover strands be labeled with a non-nucleic acid molecule that is a member of a binding pair. This will facilitate the use of the other member of the binding pair, i.e., attached to a solid support, for removal of the fuel or anti-cover strands, either alone or paired with their complementary set or cover strands. Non-limiting examples of binding pairs are ligands and their receptors, antigenic epitopes and antibodies, etc. A preferred embodiment is the labeling of fuel or anti-cover strands at one end thereof with biotin and the use of streptavidin or an avidin-type molecule as the other member of the binding pair for binding biotin.

The polynucleic acid nanomechanical device of the present invention capable of functioning as an artificial ribosome by translating a nucleic acid signal into an unrelated nucleic acid sequence includes as its components:

a plurality of $PX-JX_2$ devices capable of cycling between two topoisomeric states, PX and $JX_2$, upon sequential addition of nucleic acid fuel/unset and set strands or of nucleic acid set cover and anti-cover strands;

a collection of different sequence specific nucleic acid fuel/unset strands and set strands or a collection of different sequence specific nucleic acid set strands, cover strands, and anti-cover strands for independently setting and unsetting the topoisomeric state of each $PX-JX_2$ device;

a plurality of a nucleic acid multi-crossover motif having a coaxial structure of parallel double helices of nucleic acid strands with cohesive ends and having dyad symmetry along a central dyad axis with symmetrical wings being connected to the coaxial structure by multiple crossovers; and a collection of nucleic acid multi-crossover molecules having different nucleic acid sequences and different sequence specific cohesive ends, which nucleic acid multi-crossover molecules serve as the building blocks for assembly of specific nucleic acid sequences which bear no direct relation to the sequence specific nucleic acid set strands as nucleic acid signals.

The coaxial structure of parallel double helices of nucleic acid strands from the nucleic acid multi-crossover-motif serve to connect through cohesive ends the parallel double helices of one $PX-JX_2$ device to another along the central dyad axis formed by the parallel double helices of the $PX-JX_2$ devices and the nucleic acid multi-crossover motif. Thus, each $PX-JX_2$ device in the polynucleotide nanomechanical device of the present invention is connected to another $PX-JX_2$ device by a nucleic acid multi-crossover motif to form a linear array of alternating $PX-JX_2$ device and nucleic acid multi-crossover motif.

When referring to a plurality of a nucleic acid multi-crossover motif, it is intended that, while the structure of the motif may remain essentially the same throughout the polynucleotide nanomechanical device (the embodiment in FIGS. 2 and 5 however has a diamond motif I that is different from the other double diamond motifs II+III and IV+V merely for the purpose of facilitating identification of the correct structure using atomic force microscopy, as the motifs are different in size), the nucleic acid sequence and/or the sequence specific cohesive ends in each nucleic acid multi-crossover motif may be different. In particular, different sequence specific cohesive ends on the symmetrical wings of the nucleic acid multi-crossover motif facilitate the assembly of specific nucleic acid sequences as products of the polynucleotide nanomechanical device of the present invention by cohesion to complementary cohesive ends present on the molecules in the collection of nucleic acid multi-crossover molecules.

Each of the PX-JX$_2$ devices in the polynucleotide nanomechanical device of the present invention includes a nucleic acid paranemic crossover molecule having a four-stranded coaxial structure of flanking parallel Watson-Crick double helices of nucleic acid strands with two backbones, two pairs of ends, a plurality of major and minor grooves, a central dyad axis, and reciprocal crossovers, where two strands of a strand pair from one helix pass over to the other helix. The reciprocal crossovers flank the central dyad axis at every major and minor groove separation where two strands of a strand pair from one helix approach the central dyad axis, each of the strands being involved in a crossover at the start and end of a Watson-Crick helical turn.

Each of the PX-JX$_2$ devices is set independently between the nucleic acid paranemic crossover molecule (PX) and its JX$_2$ topoisomer through the use of nucleic acid unset and set strands or nucleic acid set, cover and anti-cover strands sequence specific for a particular PX-JX$_2$ device. The JX$_2$ topoisomer differs from the nucleic acid paranemic crossover molecule by having one pair of ends rotated relative to the other pair of ends by 180° and by having two adjacent sites where the two backbones juxtapose without the strands being involved in a crossover.

A segment of a strand from each of the strand pairs of the nucleic acid paranemic crossover molecule PX, which segment is referred to as a PX set strand and which is broken from the rest of the strand, is stripped from the nucleic acid paranemic crossover molecule by the addition of unset strands or PX cover strands complementary to the PX set strands followed by either the addition of JX$_2$ set strands or the addition of JX$_2$ anti-cover strands to convert the nucleic acid paranemic crossover molecule to its JX$_2$ topoisomer. The JX$_2$ topoisomer is converted/cycled back to the nucleic acid paranemic crossover molecule by the addition of unset strands or JX$_2$ cover strands complementary to the JX$_2$ set strands to strip the JX$_2$ set strands from the JX$_2$ topoisomer followed by either the addition of PX set strands or the addition of PX anti-cover strands.

Figure 10A:
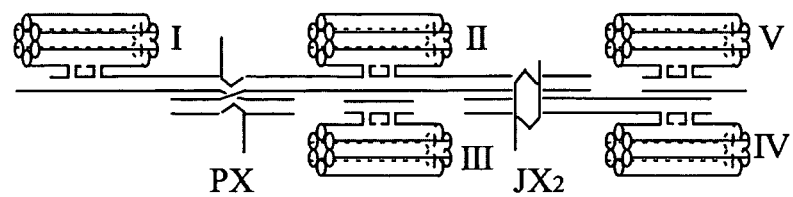
FIGS. 10A and 10B show additional embodiments of the plural PX-JX$_2$ device of FIG. 2, where the "wings" are six helical bundles (FIG. 10A) and triple crossover molecules (FIG. 10B).
Figure 10B:
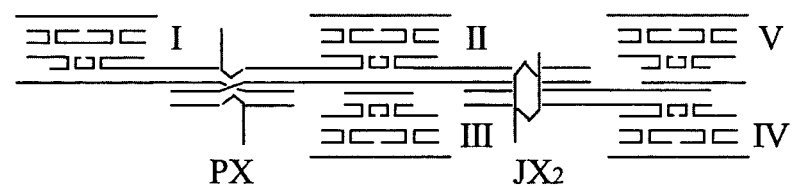

The two "wings" on each nucleic acid multi-crossover motif which are symmetrical to each other about the central dyad axis are nucleic acid multi-crossover molecules connected to the coaxial structure of the nucleic acid multi-crossover motif by multiple crossovers. Preferred embodiments of the symmetrical wings are the diamond shaped structures formed by two edge-sharing triangles shown in FIG. 2, the six-helical bundles shown in FIG. 10A, and the triple crossover (TX) molecules shown in FIG. 10B. The structures of the six-helical bundles and triple crossover TX molecules are disclosed in, for example, Mathieu et al. (2001) and LaBean et al. (2000). In each of these preferred embodiments, the cohesive ends on a double helical domain of the symmetrical wings, which double helical domain is parallel to the central dyad axis, can cohere with the nucleic acid building blocks from the collection of nucleic acid multi-crossover molecules to assemble a nucleic acid strand of a specific sequence as determined by the set strands as nucleic acid signals, the sequence specific cohesive ends on the symmetrical wings in the linear array of alternating PX-JX$_2$ devices and nucleic acid multi-crossover motifs, and the collection of nucleic acid multi-crossover molecules. Thus, based on the order in the linear array of alternating PX-JX$_2$ devices and multi-crossover nucleic acid motifs of the topoisomeric states set by the set strands as nucleic acid signals and the sequence specific cohesive ends on the double helical domain of the symmetrical wings, selected nucleic acid multi-crossover molecules from the collection of nucleic acid multi-crossover molecules are placed adjacent to each other in a specified order by cohesion between the sequence specific cohesive ends of the double helical domain of the symmetrical wings and complementary sequence specific cohesive ends of the nucleic acid multi-crossover molecules in the collection of nucleic acid multi-crossover molecules. The adjacent nucleic acid multi-crossover molecules can then be ligated together and lead to a nucleic acid strand product of specified sequence.

Preferably, the multi-crossovers in the nucleic acid molecules and motifs are double crossovers.

It should be appreciated that the terms "nucleic acid" or "polynucleic acid" refer to both DNA and RNA and hybrids of the two. The structure need not resemble anything which can theoretically be made from nature.

A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al., 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties. Non-limiting examples of nucleic acids include DNA, RNA, Peptide Nucleic Acid (PNA), and Locked Nucleic Action (LNA). A review of some nucleic acid variations, including derivatized/modified bases and other unusual bases, is presented in Freier et al. (1997).

Within a particular strand, the heterocyclic base may be entirely missing from the sugar moiety. This may be particularly desirable where the strands bend, form a junction, or where one desires fewer forces holding the strands together.

A particular strand need not have a single contiguous ribose-phosphate or deoxyribose-phosphate backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phophoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago. The term "oligonucleotide", "polynucleotide" and "nucleic acid" are intended to cover all of these structures.

In nature and the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

From a chemical standpoint, the present inventors expect to be able to couple this system with a recent method that adds reactive groups to the backbone residues of nucleotides (Zhu et al., 2003; U.S. patent application Ser. No. 10/855,893). As reported, that method adds bivalent reactive groups to each nucleotide in the backbone; a system not likely to be supported by the steric nature of a DX molecule. However, adding a reactive group, such as diamino groups or dicarboxyl groups, to the continuous chain to a few accessible sites (e.g., once per helical turn) would be independent of steric effects and can attach another detachable polymer. Such groups could be used in this context to scaffold the construction of diverse and unprecedented polymers of well-defined size and composition.

Figure 16A:
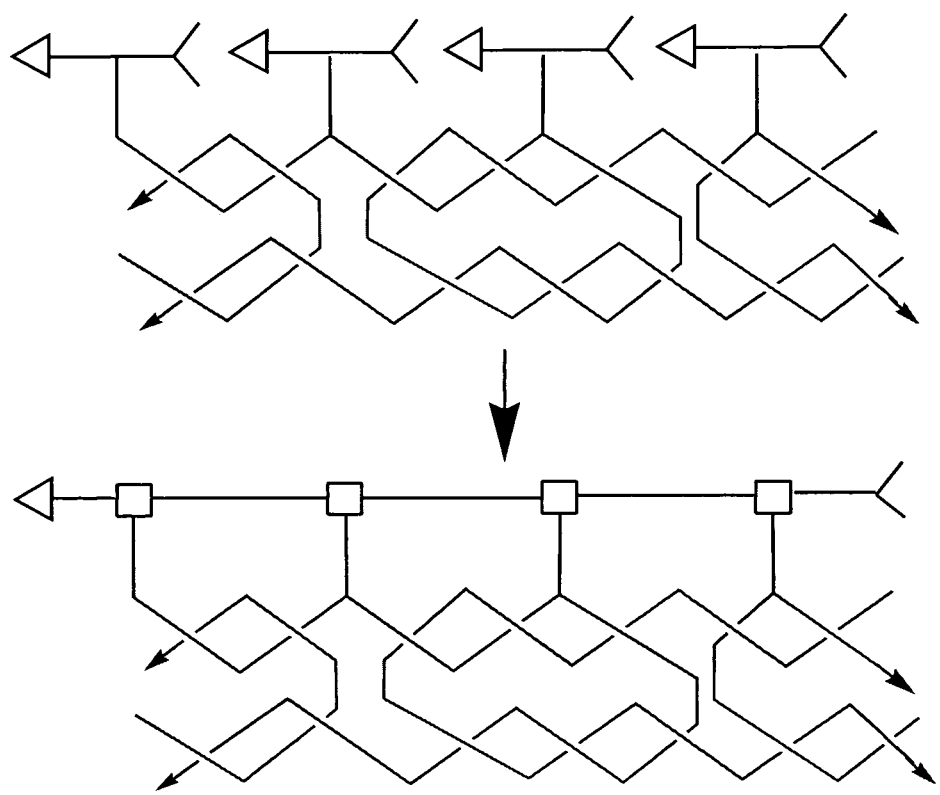
FIGS. 16A and 16B schematically show the general strategy for construction of a DX/organic oligomer building block (FIG. 16A) and the assembly of a DX/polyamide building block using diamine/dicarboxylic acid strategy (FIG. 16B).
Figure 16B:
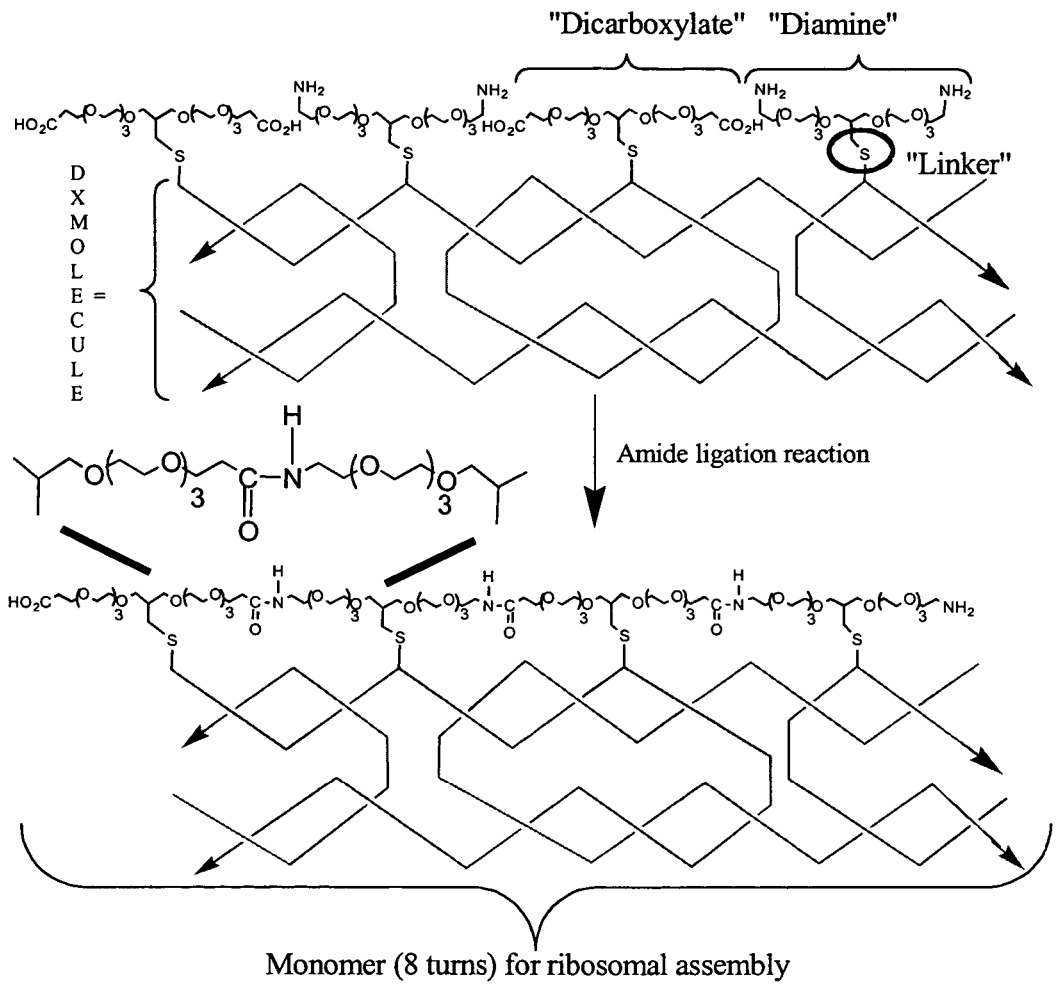

Construction of appended organic polymers can be accomplished by assembly of smaller units on the DX molecule followed by oligomerization templated by the DNA molecules, as shown in FIG. 16A. DX/organic oligomer building blocks can be constructed with one covalent attachment per turn of B-form DNA. Molecular models suggest that 34 Å/turn corresponds to approximately 30 atoms (e.g., 30 atoms in a fully anti-form alkane chain gives an end-to-end distance of 35 Å). FIG. 16B shows an embodiment based on the previously reported polyamide strategy (Zhu et al, 2003). Cassettes containing 2'-deoxy-2'-alkylthiouridine can be incorporated into DNA strands by the methods developed in the Seeman and Canary laboratories (Zhu et al 2003, Zhu et al 2002). The DX molecules will be assembled and the amides linked using peptide coupling chemistry. While FIGS. 16A and 16B show the use of the DX motif, the TX motif can also be used instead of the DX motif.

The temptation by the DNA will determine the length of the organic polymer formed. Intermolecular reactions will be several orders of magnitude slower and will essentially not be observable under the conditions of the synthesis (Gartner and Liu, 2001). The DMT-MM reagent will activate all of the carboxyl groups including the terminal one, but the only available amines are either 260 Å away or in another molecule. In either case, no reaction except the background reaction with water to regenerate the carboxyl will occur. Coupling will occur only between adjacent amines and carboxylates, not between remotely located functional groups, due to the rigidity of the DX molecule, which is even more rigid than duplex DNA (Sa-Ardyen et al., 2003).

Using these procedures, the first generation polymer 10 below can be produced where $Q_1=Q_2=$triethylene glycol and n is determined by the number of "ribosomal" cycles.

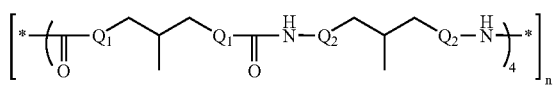

10

Various "monomers" can be prepared with varying Q moieties. Additionally, the monomer synthesis allows $Q_1$ and $Q_2$ to be different. Several examples of building blocks that may be used as Q moieties are shown below.

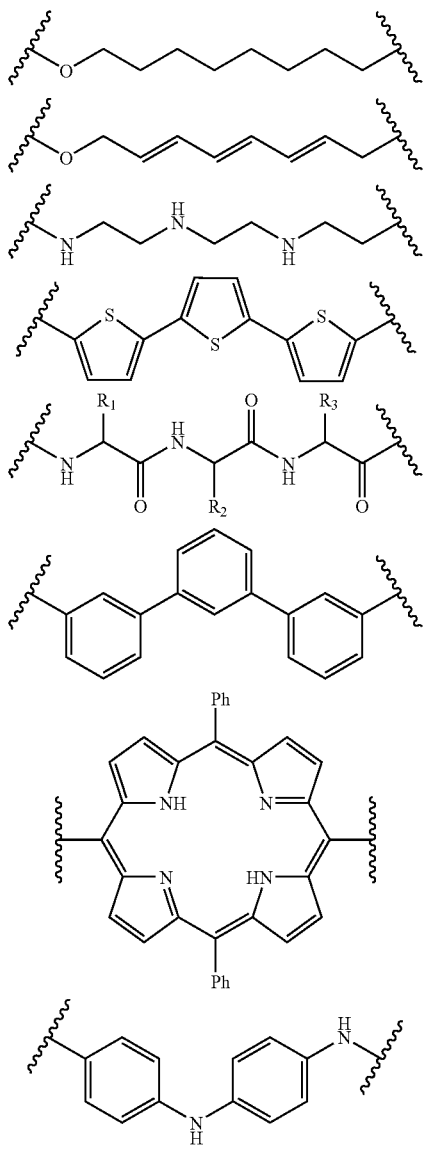

By constructing various monomers and using the ribosome protocol with the polynucleotide nanomechanical device of the present invention, a polymer with generalized formula 12 can be constructed.

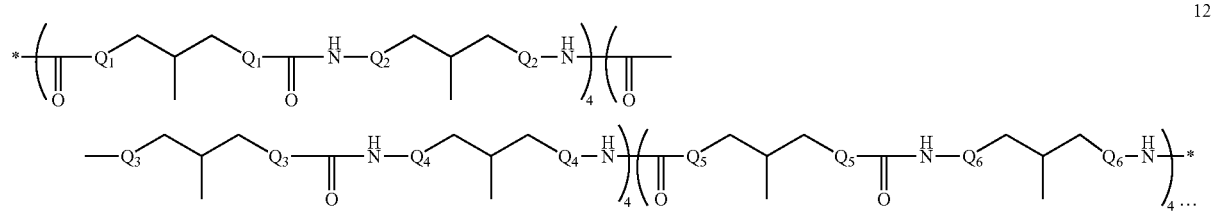

12

It is worth noting that the linkage chemistry is a point of potential variability. Additional chemistries are available for linking organic moieties together. A variety of organic reactions has been shown to be compatible with DNA (Kanan et al, 2004). In principle, such reactions could be used to link organic polymers, although they would need to be examined for compatibility in DNA automated synthesis.

In addition, the number of linkages to the DX molecule can be varied. For example, the number of connections can be reduced to one every second turn by replacing the triethylene glycol with octaethylene glycol (Fluka) in the synthesis. The connections being at the same angular point (although not being limited to every 360° turn) of a multi-crossover molecule, i.e., DX or TX molecule, are preferred. Peptide residues generated from automated synthesis are available in even greater lengths, making possible even fewer DX/polymer cross links. Even longer peptides are available using modern chemical ligation techniques (Bang and Kent, 2004). Artificial peptide residues can be incorporated into sequences generated by these protocols. The sulfide linker group could be derived from cysteine, such that after reductive cleavage of the peptide from the DNA, the cysteine residue would be converted into an alanine. Alternatively, noncovalent "sticky" groups could be used to bind the monomer organic groups to the TX molecules. Multiple, "self-sorting" host/guest pairs are available that could be used for this purpose (Mukhopadhyay et al. 2004; Poulin-Kerstien et al., 2003).

The present invention thus also provides ladder polymers capable of being assembled by the polynucleotide nanomechanical device of the present invention, where the generic structure is presented below as general formula (I).

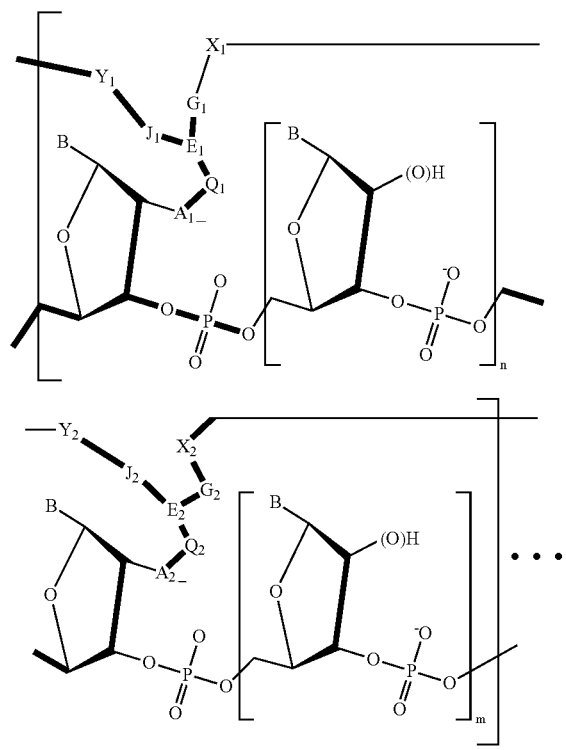

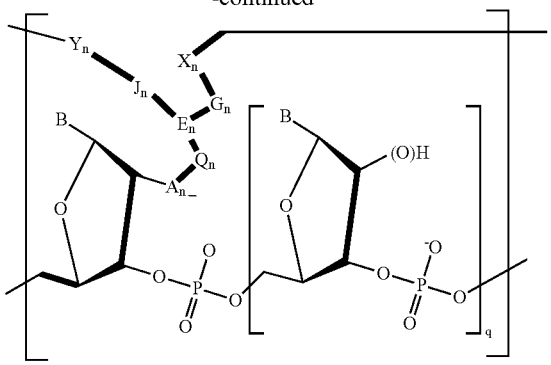

wherein

A=a Group VI element selected from the group consisting of O, S, Se, and Te;

G, J, Q=a linker group selected from the group consisting of $C_1$-$C_{18}$ branched and straight chain alkyl groups, $C_6$-$C_{24}$ substituted and unsubstituted aromatic and heteroaromatic groups having from 1-3 hetero atoms (N,S,O) or halogen substitution, —O—, —S—, carbonyl, carboxyl, —$SiR_2$—, and —$OSiR_2O$—;

B=a nucleic acid base selected from the group consisting of U, T, A, G, C, and derivatives thereof recognizable to one skilled in the art as a nucleic acid "base", and can be the same or different on different nucleotide units;

E=a symmetric or asymmetric atom center selected from the consisting of CR, N, NR+, phosphine, phosphine oxide, phosphate, phosphonate, phosphinate, phosphoramide, phosphonamide, and phosphinamide;

R=a terminal group selected from the groups consisting of H, $C_1$-$C_{18}$ branched and straight chain alkyl groups, $C_6$-$C_{24}$ substituted and unsubstituted aromatic, and heteroaromatic groups having from 1-3 hetero atoms (N,S,O) or halogen substitution;

Pair XY=bonding sites such that X can be caused to form a chemical bond with Y by the techniques of organic synthesis;

The subscripts, e.g., 1, 2, n, etc., denote not only a sequence in the chain of units (Brackets) forming a copolymer but also denote that the moieties designated by the letters, e.g., B, X, Y, etc., may or may not be the same from unit to unit.

The X-Y pair preferably form amide, ester, phosphoester, or alkene bonds, such as from electrocyclic reactions. Most preferably, the X=Y pair forms an amide bond.

The polymer produced from desulfurization reaction of the polymer of formula (I) is presented below as formula (II)

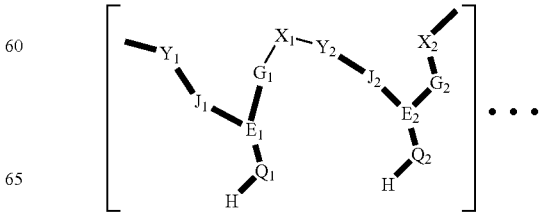

-continued

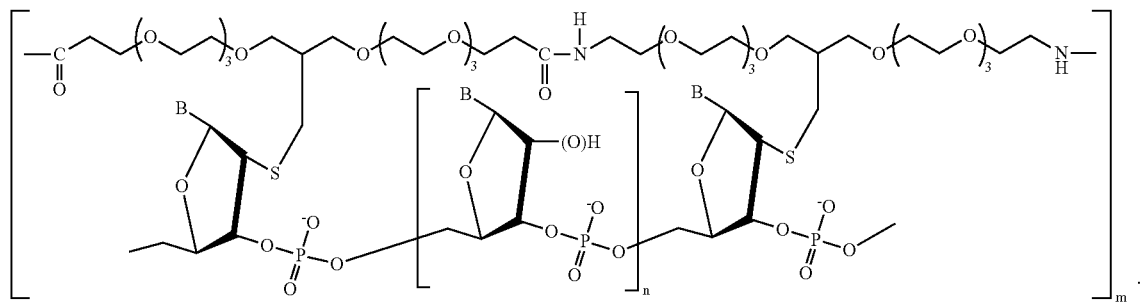

A preferred embodiment of the polymer of formula (I) is a DNA/polyamide polymer having the structure of formula (III) below.

The polymer that would be produced from desufurization reaction of formula (III) is shown below as formula (IV).

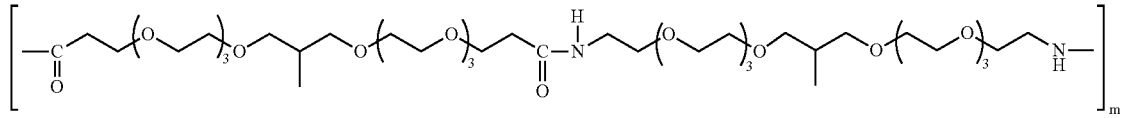

The present invention further provides a process for producing the polymer of formula (II) by operating the polynucleic acid nanomechanical device of the present invention to assemble a polymer of formula (I) and then forming/producing the polymer of formula (II) by desulfurization reaction.

Having now generally described the invention, the same will be more readily understood through reference to the following examples which are provided by way of illustration and is not intended to be limiting of the present invention.

Example 1

Materials and Methods

Figure 3:
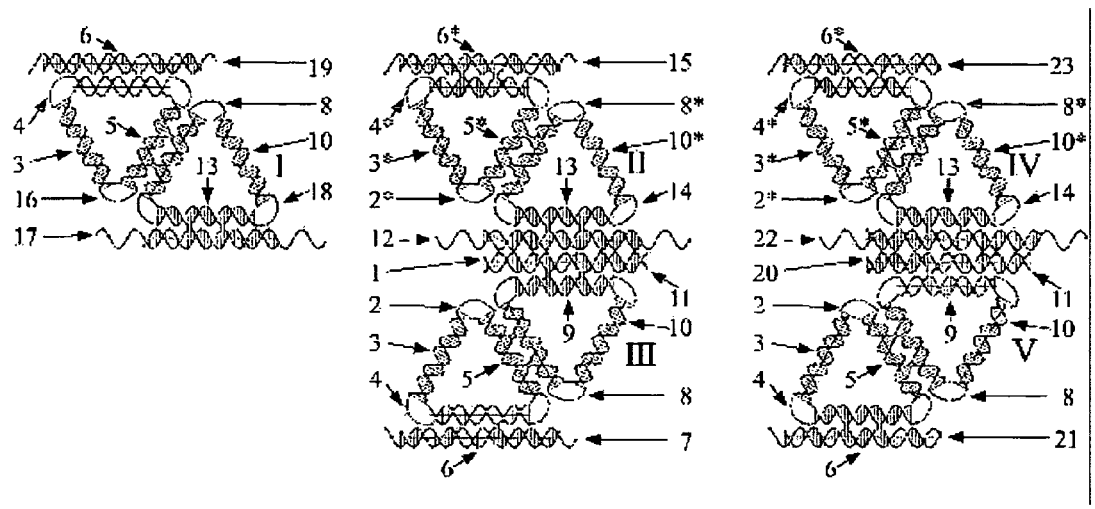
FIG. 3 shows the strand numbering for the diamond components in FIG. 2. Strands used twice in the same physical unit are labeled with an asterisk.
Figure 4:
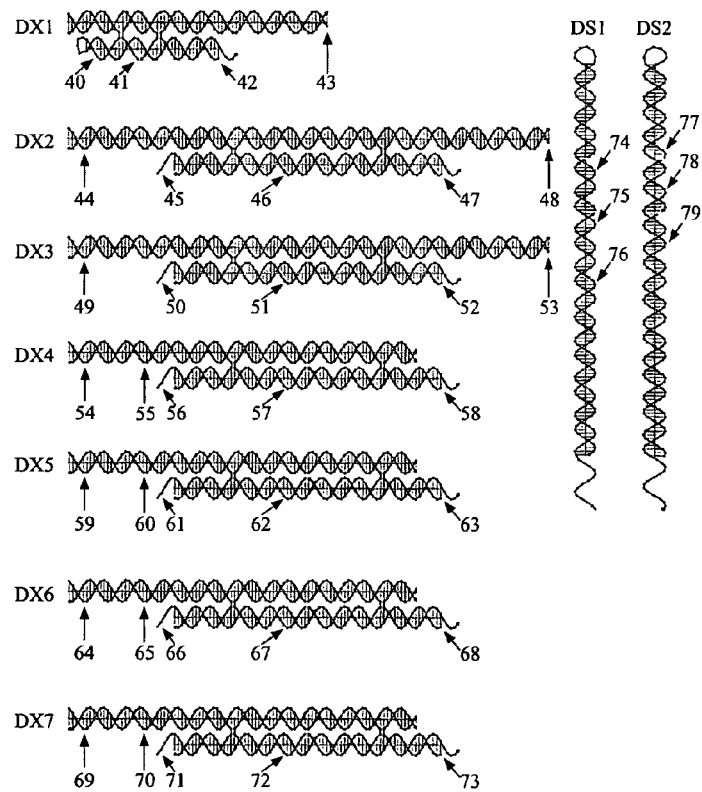
FIG. 4 shows the strand numbering for the DX and DS components used in FIG. 5.

Device Assembly. The strands were designed using the program SEQUIN (Seeman, 1990). The component strands of diamonds I, II, III, IV and V (FIGS. 2 and 3; SEQ ID NOs:1-23) were dissolved separately to a concentration of 1 µM in a solution containing 40 mM Tris, pH 8.0, 20 mM acetic acid, 2 mM EDTA and 12.5 mM magnesium acetate (TAEMg), and the mixtures were heated to 90° C. and cooled slowly to 4° C. Diamonds II and III were then combined, as were diamonds IV and V, and these mixtures were heated to 48° C. and cooled slowly to 4° C. In the following, diamond I is termed U1, complex II+III is termed U2 and complex IV+V is termed U3. The component strands of PX1, PX2, DX1, DX2, DX3, DX4, DX5, DX6, DX7, DS1, and DS2 (FIG. 4; SEQ ID NO:40-79) were dissolved separately to a concentration of 2 µM in the same solution. These mixtures were heated to 90° C. (5 min), and cooled as follows: 65° C. (30 min), 45° C. (30 min), 37° C. (30 min), 4° C. (30 min). U1, PX1, U2, PX2, and U3 were combined, heated to 40° C. and cooled slowly to 4° C.

Setting the Device State. Unset strands were added to the solution and the solution was kept at 20° C. for 3 hours; the solution was treated with streptavidin beads at 20° C. for 30 minutes to remove the set-strand/unset-strand duplexes. At this point, the set strands for the target $JX_2$ or PX states were added to the solution and kept at 20° C. for 3 hours to establish the device conformation.

Preparing and Purifying the Assembly Complex. DS1 and DX complexes 1-7 were added to the solution. The mixture was heated with the following thermo-cycling protocol: 35° C. (10 min), 33° C. (10 min), 30° C. (10 min), 25° C. (10 min), 20° C. (10 min) for 15 cycles. The solution was treated with magnetic streptavidin beads at 20° C., 30 minutes to bind devices with an intact left-hand side. Failed assemblies were washed away and the solution containing the beads were replaced with a new solution containing 40 mM Tris, pH 8.0, 20 mM acetic acid, 2 mM EDTA, 12.5 mM magnesium acetate, 50 mM potassium acetate and 1 mM DTT. Ten units of SmaI restriction endonuclease (New England BioLabs, Beverly, Mass.) were added and the solution was incubated at 20° C. for 1 hour to release the target assembly, and the beads then removed from the solution. DS2 was then added, and the solution was incubated at 20° C. for 2 hr, followed by magnetic streptavidin bead treatment at 20° C. for 30 minutes only those with an intact right-hand side should be bound. The solution was replaced with a new solution containing 40 mM Tris, pH 8.0, 20 mM acetic acid, 2 mM EDTA, 12.5 mM magnesium acetate, 50 mM potassium acetate and 1 mM DTT. Ten units of ApaI restriction endonuclease (New England BioLabs) were added, and the solution was incubated at 20° C. for 1 hour and the magnetic beads were removed.

Ligation and Analysis. The solution was brought to 1 mM in ATP and 10 units of T4 polynucleotide ligase (USB) were added. The ligation proceeded at 16° C. for 16 hours. Following ligation, the solution was heated at 90° C. for 5 minutes, and the ligation products were purified using 6% denaturing PAGE. The ligation products were sequenced to establish the correct assembly. A few missed or unknown bases are noted in the experimental sequencing, but these are far from the ligation points, and likely represent errors in the sequencing procedure.

Results

Figure 5:
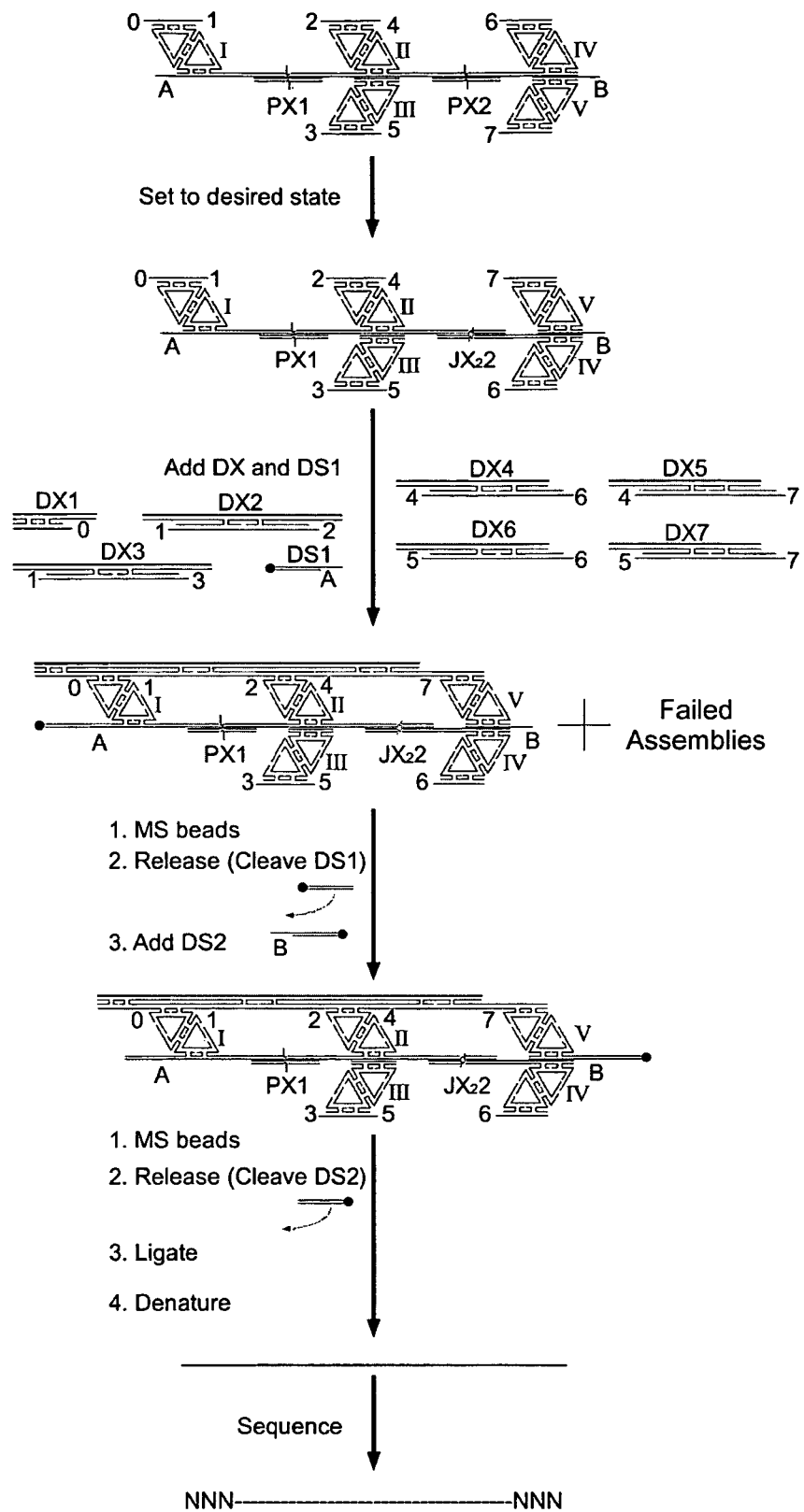
FIG. 5 schematically shows a flowchart of the operation of the plural PX-JX$_2$ device. The initial assembly of the device is shown at the top, similar to the structure in FIG. 2. 'A' and 'B' indicate sticky ends used in purification. The next step entails setting the state of the device; the one illustrated here is PX1, JX$_2$2, so the right assembly is flipped, and the DX molecules that fit into the 1-2 (DX2) and 4-7 (DX5) slots will be selected. The collection of DX molecules are all added to the solution, along with an initiator DX1 and a biotinylated double strand, DS1, complementary to A. The correct ones bind to the top, including the initiator DX1. Failed assemblies are removed by streptavidin magnetic beads that bind biotin on DS1. Following left-side purification by streptavidin magnetic beads, and release by cleaving DS1, a second right-side purification is achieved similarly using DS2 and adding streptavidin magnetic beads again. The purified complex is then ligated, and the continuous strand is denatured, purified, and sequenced.
Figure 6:
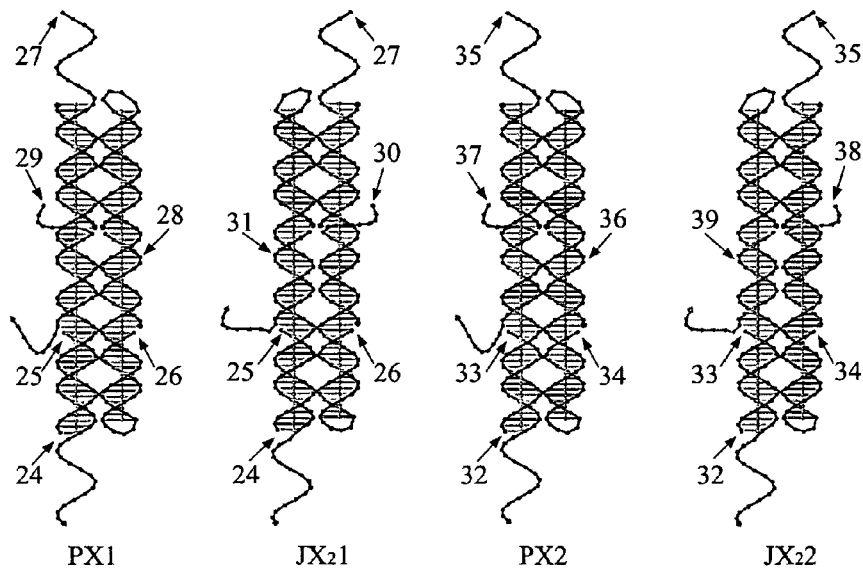
FIG. 6 shows the strand numbering for the PX-JX$_2$ devices (in both PX and JX$_2$ states) in FIGS. 2 and 5.
Figure 7:
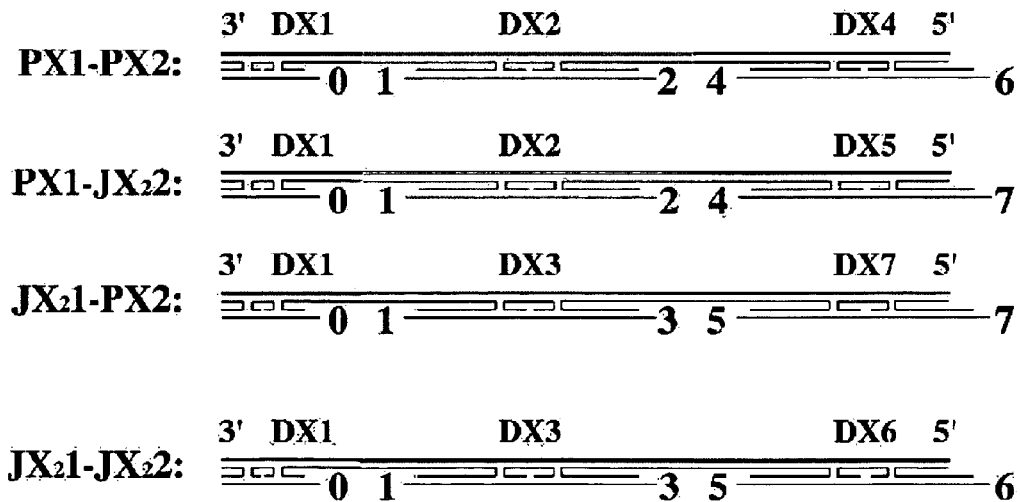
FIG. 7 shows the four potential ligated product DX structures. The continuous strands across the top are the final products that are sequenced.

FIG. 5 illustrates the flow-chart for the experiments performed here. First, the device is constructed with both PX-JX$_2$ machines in the PX state (FIG. 6; SEQ ID NOs:24-39). Unset strands (SEQ ID NOs:80-87), followed by specific set strands are then added to the device, setting its state. The complete set of DX molecules is added to the solution, and the correct ones bind in the correct sites between the diamond structures, as dictated by the sticky ends. In addition, an 'initiator' DX is bound on the top of the leftmost double diamond. Following ligation, the DX molecules are dissociated, the target strand is isolated, and its sequence is determined. Its target length is longer than any other strand in the system, so it is easy to isolate from failure products and fortuitous molecules that bind to the opposite (bottom) side of the device. FIG. 7 shows the way that the selection of set strands directs the synthesis of different products, in the same way that different mRNA molecules direct the synthesis of different polypeptide chains. It is important to recognize that the top strand (SEQ ID NOs:88-91) in each of the four different combinations (products) shown in FIG. 7 is synthesized as a function of the signal sequences of DNA (set strands), to which they are totally unrelated, that set the states of the DX-JX$_2$ devices.

FIGS. 8A and 8B show a non-denaturing gel in which each of the 22 strands of a wing component is labeled individually. The uniform nature of the gel demonstrates that the complex contains all of the strands, and that no strand partially denatures from it. FIGS. 8B and 8D contain atomic force micrograph (FIG. 8C) and a zoom (FIG. 8D) of it showing purification of the device in the absence of DX molecules. Each molecule contains two large components, corresponding to the double diamond wings, and a smaller one on the end, corresponding to the single diamond that supports the initiator DX. The product strands from the four different combinations are shown in a denaturing gel in FIG. 9. Numerous ligation failures are evident, but the target molecules containing 307 nucleotides are well represented on the gels. In each case, the target molecule contains the expected sequence.

The present inventors have now produced a device that translates a DNA signal into an unrelated sequence. The connection between the signals and the products (the 'genetic code' for this system) has been established so that there is no transcriptional relationship between them. It is evident that this simple device prototypes an arbitrary, but general, encryption method (Landweber et al., 1997). In addition, this type of device would serve as the basis for a finite-state machine with variable input (Jonoska et al., 2004).

Example 2

RNA molecules do not fit well into the PX-JX$_2$ molecules that constitute the most robust sequence-dependent devices. Consequently, a cover-strand approach was developed to gain the strength of both the robustness of DNA and the logical production of RNA (i.e., RNA molecules transcribed in response to a signal in a DNA device). In this approach, the control strands that set the state of the device to be PX or JX$_2$ contain the information to set either state. They are made of DNA. One can select the desired state by covering up the part corresponding to the state that is not desired. The cover strands are made of RNA.

Figure 11:
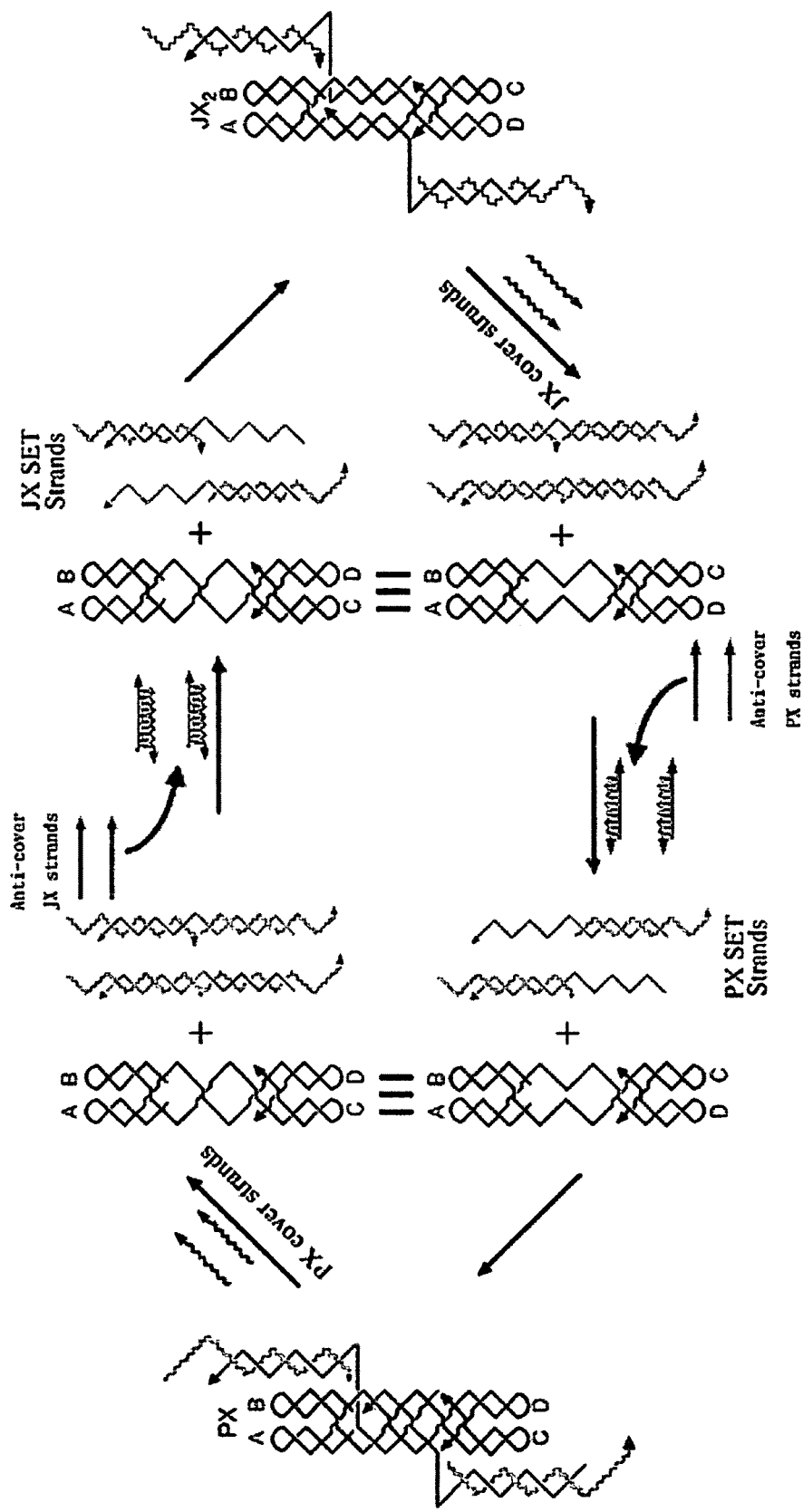
FIG. 11 schematically shows the machine cycle of a PX-JX$_2$ device similar to FIG. 1, except that the interconversion between the PX and JX$_2$ states is accomplished with PX and JX$_2$ set strands, RNA cover and anti-cover strands, and control strands (each with a PX portion and a JX$_2$ portion). The squiggly lines represent RNA.

The cycle involving RNA cover strands is shown in FIG. 11. The squiggly lines represent RNA. The two states are on the ends. The cycle proceeds from the PX state by adding the cover strands that cover up the PX set-strand portions of the control strands. This leaves a naked frame. The second step is to uncover the covered part of the control strands corresponding to the JX$_2$ state with JX$_2$ anti-cover strands. The JX$_2$ state now forms with JX$_2$ set strands, which are control strands with the PX portion still covered up by PX cover strands. The uncovering is done by the traditional method with overhangs.

Figures 12A, 12B:
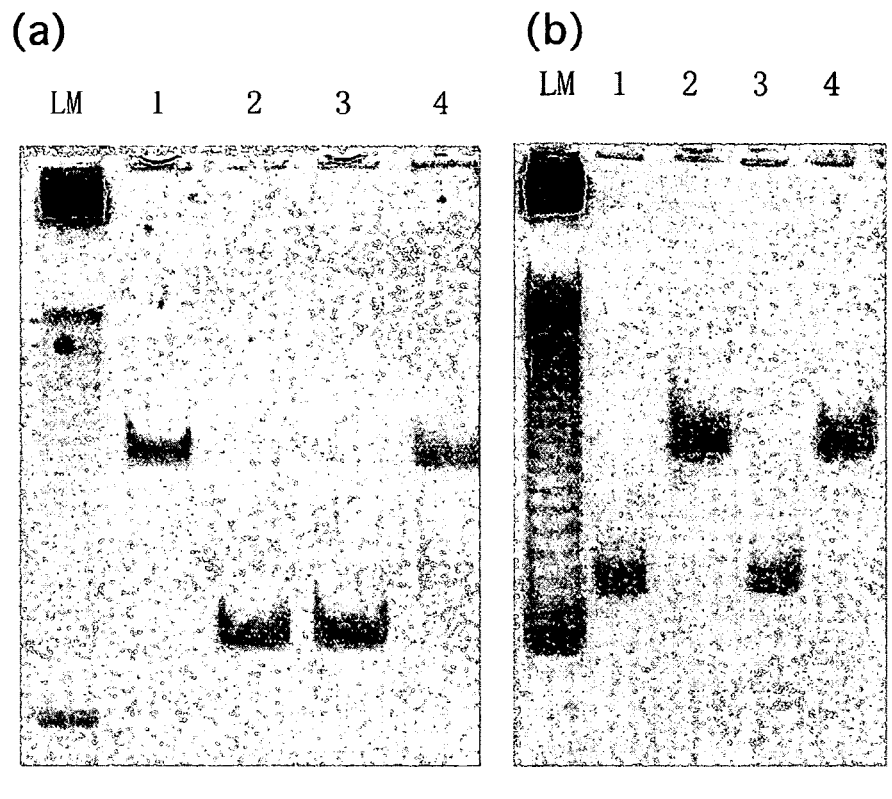
FIGS. 12A and 12B are 6% non-denaturing polyacrylamide gels showing components of the PX-JX$_2$ device of FIG. 11 in operation.

FIG. 12A is a gel showing the components of the PX-JX$_2$ device in operation. This is a 6% non-denaturing polyacrylamide gel, run at 20° C. and stained with stains-all dye (Sigma E-7762). The lane LM contains 10 bp linear length markers. Device strand sequences have been designed using the program SEQUIN. All the DNA strands are synthesized by routine phosphoramidite techniques and gel purified in RNase free condition. All the RNA strands are ordered from IDT Inc. Set strands and framework of the device are hybridized from 90° C. to 20° C. for 48 hrs, separately. Then, set strands are mixed with the DNA framework. The mixture is hybridized from 37° C. to 20° C. for 12 hrs. Lane 1 contains the device (1 uM) assembled with JX$_2$ set strands and lane 3 contains the device (1 uM) assembled with PX set strands. Lane 2 contains the products transferred from the material in lane 1 by pulling the set strands out by JX$_2$ cover strands and removing the PX cover strands. Likewise, lane 4 contains the products transferred from the material in lane 3 by pulling the set strands out by PX cover strands and removing the JX$_2$ cover strands. Note the absence of extraneous products in lanes 2 and 4, indicating the robustness of these transformations.

FIG. 12B is a gel showing the cycling of the PX-JX$_2$ device between the PX and JX$_2$ states through 4 steps. Lane 1 is the initial PX conformation, and lanes 2 to 4, respectively, show alternating transformations to the other state. Cover strands were added to the preformed PX or JX$_2$ at 20° C. and kept at 20° C. for 120 min. Then JX$_2$ or PX anti-cover strands were added at 20° C. for 6 hrs; at the same time, the uncovered JX$_2$ or PX set strands can form JX$_2$ or PX molecules with the DNA frame molecules. After the transition of device conformation is finished, the mixture was treated with streptavidin beads at 20° C. for 30 min to remove the cover-strand/anti-cover-strand duplexes. The addition of cover strands, followed by anti-cover strands, was then repeated two times. The strand sequences from gel evidence of the operation of the device is presented in Table 1 below.

TABLE 1

SEQUENCES FOR GEL EVIDENCE OF
THE OPERATION OF THE DEVICE

| | |
|---|---|
| COVER-JX-1 | SEQ ID NO:92 |
| COVER-PX-1 | SEQ ID NO:93 |
| COVER-JX-2 | SEQ ID NO:94 |
| COVER-PX-2 | SEQ ID NO:95 |
| ANTI-COVER-JX-1 | SEQ ID NO:96 |
| ANTI-COVER-PX-1 | SEQ ID NO:97 |
| ANTI-COVER-JX-2 | SEQ ID NO:98 |
| ANTI-COVER-PX-2 | SEQ ID NO:99 |
| SET-1 | SEQ ID NO:100 |
| SET-2 | SEQ ID NO:101 |
| LH-1 | SEQ ID NO:102 |
| LH-2 | SEQ ID NO:103 |

Figure 13:
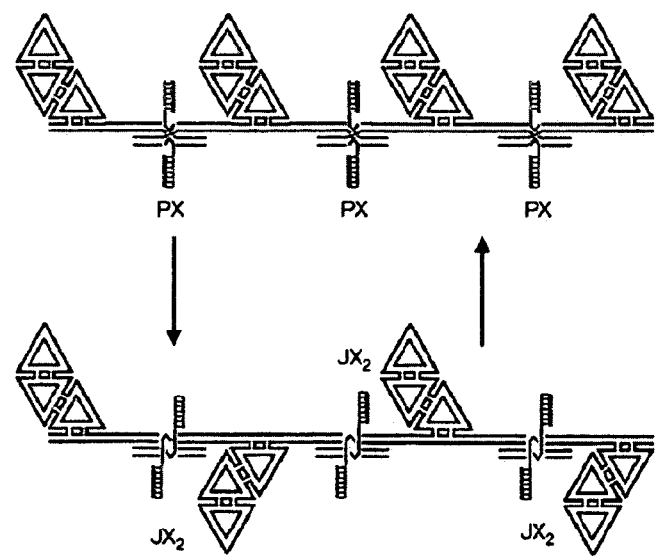
FIG. 13 schematically shows a system where the interconversion between the PX and JX$_2$ states is detected by the different signature for each state using atomic force microscopy (AFM).
Figures 14A, 14B, 14C, 14D:
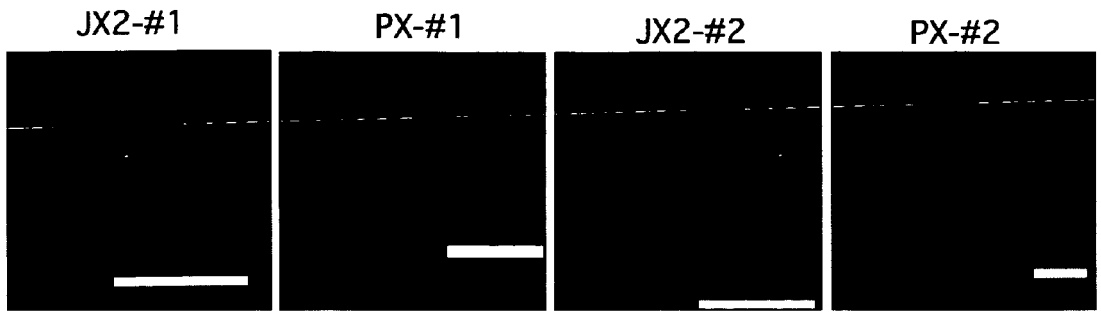
FIGS. 14A-14D are AFM images of control PX (FIGS. 14B and 14D) and JX$_2$ (FIGS. 14A and 14C) states. All whites bars represent 40 nm.

Further evidence for the PX-JX$_2$ operation of the device were obtained from atomic force microscopy (AFM). The system used is illustrated in FIG. 13 where the two different states have different signatures, visible in the AFM, as schematized in FIG. 13. In the JX$_2$ state, there is a zigzag pattern and in the PX state there is a parallel pattern. The experimental protocol is as follows. The DNA frame molecules of the initial species are produced by annealing their constituent single strands from 90° C. to 20° C. in a Thermos over a period of 5 days. Meanwhile, the set strands are hybridized from 90° C. to 20° C. for 2 days. After annealing, the set strands and the DNA frame are mixed, heated to 37° C. and cooled to 20° C. for 12 hrs. The one-dimensional arrays of these half-hexagon-plus-device units cohere by way of 11-nucleotide sticky ends. RNA cover strands were added to the preformed PX or $JX_2$ at 20° C. and kept at 20° C. for 120 min. Then $JX_2$ or PX anti-cover strands were added at 20° C. for 6 hrs; at the same time, the uncovered $JX_2$ or PX set strands could form $JX_2$ or PX molecules with the DNA frame molecules. After the transition of device conformation is finished, the mixture was treated with streptavidin beads at 20° C. for 30 min to remove the cover-strand/anti-cover-strand duplexes. The sequences used in the operation of PX-$JX_2$ for AFM imaging is presented in Table 2 below.

TABLE 2

SEQUENCES FOR AFM IMAGING

| | |
|---|---|
| CJX-1D-1 | SEQ ID NO:104 |
| CPX-1D-1 | SEQ ID NO:105 |
| CJX-1D-2 | SEQ ID NO:106 |
| CPX-1D-2 | SEQ ID NO:107 |
| Anti-CJX-1D-1 | SEQ ID NO:108 |
| Anti-CPX-1D-1 | SEQ ID NO:109 |
| Anti-CJX-1D-2 | SEQ ID NO:110 |
| Anti-CPX-1D-2 | SEQ ID NO:111 |
| Set-1D-1 | SEQ ID NO:112 |
| Set-1D-2 | SEQ ID NO:113 |
| Strand-1d-1 | SEQ ID NO:114 |
| Strand-1d-3 | SEQ ID NO:115 |
| Strand-1d-4 | SEQ ID NO:116 |
| Strand-1d-5 | SEQ ID NO:117 |
| Strand-1d-7 | SEQ ID NO:118 |
| Strand-1d-8 | SEQ ID NO:119 |
| Strand-1d-9 | SEQ ID NO:120 |
| Strand-1d-10 | SEQ ID NO:121 |
| Strand-1d-11 | SEQ ID NO:122 |
| Strand-1d-12 | SEQ ID NO:123 |
| Strand-1d-13 | SEQ ID NO:124 |
| Strand-1d-14 | SEQ ID NO:125 |
| Strand-1d-15 | SEQ ID NO:126 |
| Strand-1d-16 | SEQ ID NO:127 |
| Strand-1d-17 | SEQ ID NO:128 |

Figures 15A, 15B, 15C:
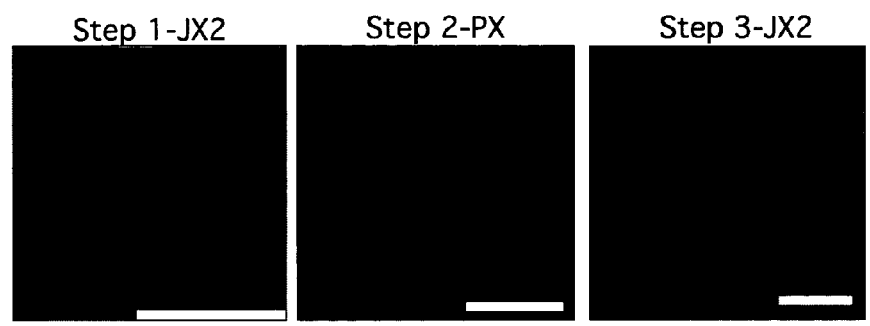
FIGS. 15A-15F are AFM images showing the steps of the cycle from JX$_2$ (FIG. 15A) to PX (FIG. 15B) and back to JX$_2$ (FIG. 15C). The other cycle is also shown from PX (FIG. 15D) to JX$_2$ (FIG. 15E) and back to PX (FIG. 15F). All white bars represent 40 nm.
Figures 15D, 15E, 15F:
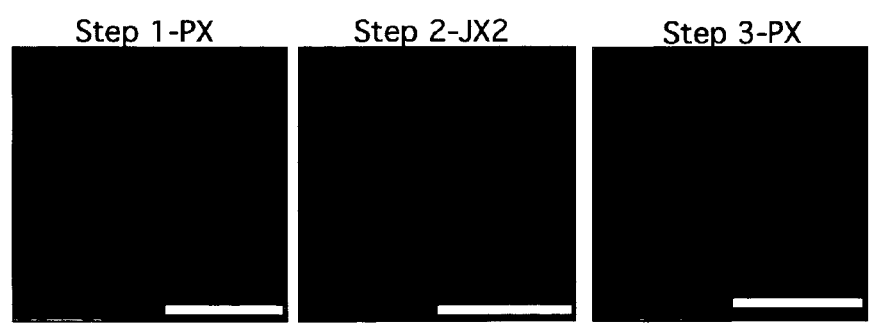

The first series of AFM (FIGS. 14A-14D) is a set of controls that are not switched, just to show what a PX and a JX looks like. Cycling from $JX_2$ to PX and back to $JX_2$ is shown in FIGS. 15A-15C, where the observed states are evident. The other cycle, from PX to $JX_2$ and back to PX is shown in FIGS. 15D-15F. It is again clear from the images that the expected transition has occurred.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Bang, D., Kent, S. B. H., A one-pot total synthesis of crambin, *Angew. Chem. Int. Ed.,* 43:2534-8 (2004)

Fu, T.-J. & Seeman, N. C., DNA double crossover structures, *Biochem.* 32, 3211-3220 (1993).

Freier S. and Altmann K.-H., The ups and downs of nucleic acid duplex stability: structure-stability studies on chemically-modified DNA:RNA duplexes, *Nucleic Acids Research,* 25:4429-4443 (1997)

Gartner, Z. J., Liu, D. R., The generalitiy of DNA-templated synthesis as a basis for evolving non-natural small molecules, *J. Am. Chem. Soc.,* 123:6961-6963 (2001)

Jonoska, N., Liao, S. & Seeman, N. C., Finite State Machines with Variable Input, *Aspects of Molecular Computing, Lecture Notes in Computer Science,* Springer-Verlag, Berlin, 2340:219-240 (2004).

Kanan, M. W., Rozeman, M. M., Sakurai, K., Snyder, T. M., Liu, D. R., Reaction discovery enabled by DNA-templated synthesis and in vitro selection, *Nature,* 431:545-549 (2004)

LaBean T., Yan H., Kopatsch J., Liu F., Winfree E., Reif J. H. and Seeman N. C., The Construction of DNA Triple Crossover Molecules, *Journal of the American Chemical Society* 122:1848-1860 (2000).

Landweber, L. F., Lipton, R. J. & Rabin, M. O., DNA$^2$DNA Computations: A Potential "Killer App?", *Proceedings of the 3rd DIMACS Meeting on DNA-Based Computers, University of Pennsylvania, June 23-25, 1997*, (eds. H. Rubin and D. Wood), 161-172 (American Mathematical Society, Providence, R.I., 1997).

Mathieu F., Mao C., Seeman N. C., *Journal of Biomolecular Structure & Dynamics*, 18:907 (2001).

Mukhopadhyay, P., Wu, A., Isaacs, L., Social self-sorting in aqueous solution, *J. Org. Chem.*, 69:6157-6164 (2004)

Piccirilli et al., *Nature* 343:33-37 (1990)

Poulin-Kerstien, A. T. and Dervan, P. B. "DNA-Templated Dimerization of Hairpin Polyamides," *J. Am. Chem. Soc*, 125:15811-21. (2003)

Sa-Ardyen, P., Vologodskii A. V.; Seeman, N. C., The Flexibility of DNA Double Crossover Molecules. *Biophysical Journal* 84, 3829-3837 (2003)

Seeman, N. C., De novo design of sequences for nucleic acid structure engineering, *J. Biomol. Struct. & Dyns.* 8:573-581 (1990).

Shen, Z., Yan, H., Wang, T. & Seeman, N. C., Paranemic Crossover DNA: A Generalized Holliday Structure with Applications in Nanotechnology *J. Am. Chem. Soc.* 126: 1666-1674 (2004).

Sherman, W. B. & Seeman, N. C., A precisely controlled DNA biped walking device, *NanoLett.* in press, (2004).

Simmel, F. C. & Yurke, B., A DNA-based molecular device switchable between three distinct mechanical states, *Appl. Phys. Lett.* 80, 883-885 (2002).

Simmel, F. C. & Yurke, B., Using DNA to construct and power a nanoactuator, *Phys. Rev. E.* 63, Art. No. 041913 (2001).

Yan, H. & Seeman, N. C., Edge-sharing Motifs in DNA Nanotechnology. *J. Supramol. Chem.* 1, 229-237 (2001).

Yan, X., Zhang, X., Shen, Z. & Seeman, N. C., A robust DNA mechanical device controlled by hybridization topology, *Nature* 415, 62-65 (2002).

Yurke, B., Turberfield, A. J., Mills, A. P., Jr., Simmel, F. C. & Neumann, J. L, A DNA-fueled molecular machine made of DNA, *Nature* 406, 605-608 (2000).

Zhu, L., dos Santos, O, Seeman, N. C., Canary, J. W., Reaction of N3-Benzoyl-3',5'-O-(di-tert-butylsilanediyl)uridine with hindered electrophiles: Intermolecular N3 to 2'O protecting group transfer, *Nucleotides, nucleosides, and Nucl. Acids*, 21:723-735 (2002)

Zhu, L., Lukeman, P. S., Canary, J. W. & Seeman, N. C., Nylon/DNA: Single-stranded DNA with covalently stitched nylon lining, *J. Am. Chem. Soc.* 125, 10178-10179 (2003).

---

What is claimed is:

1. A polynucleic acid polymer, comprising the general formula (I)

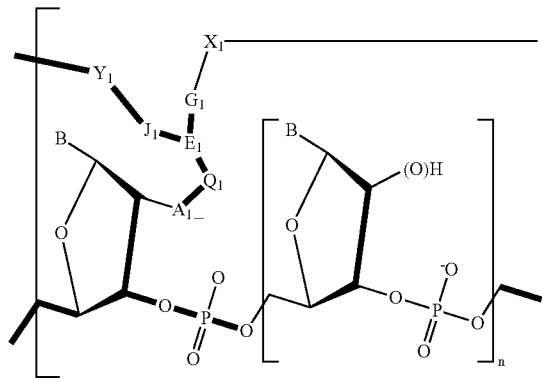

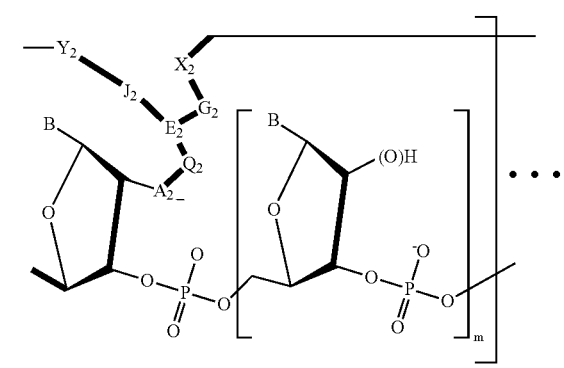

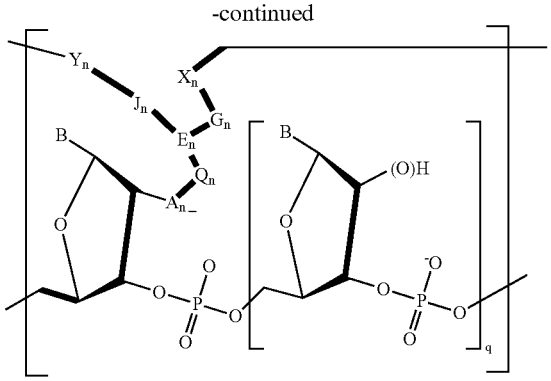

wherein:

A=a Group VI element selected from the group consisting of O, S, Se, and Te;

G, J, Q=a linker group selected from the group consisting of $C_1$-$C_{18}$ branched and straight chain alkyl groups, $C_6$-$C_{24}$ substituted and unsubstituted aromatic and heteroaromatic groups having from 1-3 hetero atoms (N,S, O) or halogen substitution, —O—, —S—, carbonyl, carboxyl, —$SiR_2$—, and —$OSiR_2O$—;

B=a nucleic acid base selected from the group consisting of U, T, A, G, C, and derivatives thereof, and can be the same or different;

E=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, $C_1$-$C_{18}$ branched and straight chain alkyl groups, $C_6$-$C_{24}$ substituted and unsubstituted aromatic and heteroaromatic groups having from 1-3 hetero atoms (N,S, O) or halogen substitution; and Pair XY=bonding sites such that X forms a covalent bond with Y by the techniques of organic synthesis.

2. The polymer of claim 1, comprising formula (III)
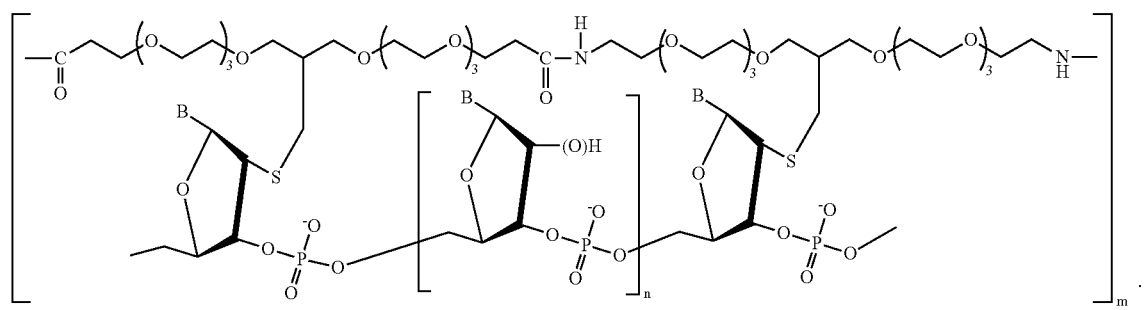
* * * * *

SEQUENCE LISTING

```
<160> NUMBER OF SEQ ID NOS: 128

<210> SEQ ID NO 1
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1

<400> SEQUENCE: 1
gatcggtgct catgtgtatg gacgctacgg gaccgcagta cggcacgttg ctatcgctca    60
atgc                                                                 64

<210> SEQ ID NO 2
<211> LENGTH: 70
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2

<400> SEQUENCE: 2
gtactagcag tttttttcgcg gtcacaccgt acagcatttt ttgtgcatgg caccgtgcac    60
atggtcgtcg                                                           70

<210> SEQ ID NO 3
<211> LENGTH: 90
<212> TYPE: DNA
<213> ORGANISM: Artificial
<220> FEATURE:
<223> OTHER INFORMATION: Synthetic
<220> FEATURE:
<221> NAME/KEY: misc_feature
```

<223> OTHER INFORMATION: Strand 3

<400> SEQUENCE: 3
cgtcgtatct gacgcatggg acgatgatgg acctacgatc cgtagattgg actgttgacc    60
tgtgaccgcg ctgctagtac gtctgtcatc                                      90

<210> SEQ ID NO 4
<211> LENGTH: 56
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4

<400> SEQUENCE: 4
gagatcgccg agcgccgtca cccatgcgtc tttttagat acgacggatg acagac         56

<210> SEQ ID NO 5
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5

<400> SEQUENCE: 5
aacgtggtca acagtggtgc                                                 20

<210> SEQ ID NO 6
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6

<400> SEQUENCE: 6
atcgtggcat taccaccatc                                                 20

<210> SEQ ID NO 7
<211> LENGTH: 60
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7

<400> SEQUENCE: 7
gtccagacgg tagtctgctt cagcctggta atgcctgacg gcgctcggcg atctccgctt    60

<210> SEQ ID NO 8
<211> LENGTH: 77
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8

```
<400> SEQUENCE: 8
gtgccgcgca ttttttagtt ggctcaccaa tctacgtttt ttgatcgtag gtggctgaag     60
cagactaccg tctggac                                                   77

<210> SEQ ID NO 9
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9

<400> SEQUENCE: 9
ctacacccgt agcgtggcgt                                                20

<210> SEQ ID NO 10
<211> LENGTH: 90
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10

<400> SEQUENCE: 10
gacaatgacg ggcagtatcc tgtagacgcc tgccatgcac tgctgtacgg acgttgcacc     60
tgagccaact tgcgcggcac ggatgtgcgc                                     90

<210> SEQ ID NO 11
<211> LENGTH: 58
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11

<400> SEQUENCE: 11
gatccacgtg cagctatgcg gtggatactg ccttttttcg tcattgtcgc gcacatcc       58

<210> SEQ ID NO 12
<211> LENGTH: 68
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12

<400> SEQUENCE: 12
gtcatagttc agtgtcacga acgactgcgt acacggacag cgcaggactg tctagctcca     60
gtgggatc                                                             68

<210> SEQ ID NO 13
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
```

<223> OTHER INFORMATION: Strand 13

<400> SEQUENCE: 13
ctacacctgc gctgtggcgt                                              20

<210> SEQ ID NO 14
<211> LENGTH: 58
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 14

<400> SEQUENCE: 14
tagcacactg gcgtacgaca gtggatactg ccttttttcg tcattgtcgc gcacatcc    58

<210> SEQ ID NO 15
<211> LENGTH: 60
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 15

<400> SEQUENCE: 15
gaccagacgg tagtctgctt cagcctggta atgcctgacg gcgctcggcg atctctaggc  60

<210> SEQ ID NO 16
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 16

<400> SEQUENCE: 16
gtactagcag ttttttcgcg gtcacaccgt acagcatttt ttgtgcatgg caccgactat  60
gtcgatc                                                           67

<210> SEQ ID NO 17
<211> LENGTH: 73
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 17

<400> SEQUENCE: 17
gtaacatgat tagcggatcg acatagtcgg acagcgcagg acacgctggc taccatacat  60
cagtcagtgt tcg                                                    73

<210> SEQ ID NO 18
<211> LENGTH: 54
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 18

<400> SEQUENCE: 18
gtatggtagc cagcgtgtgg atactgcctt ttttcgtcat tgtcgcgcac atcc            54

<210> SEQ ID NO 19
<211> LENGTH: 60
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 19

<400> SEQUENCE: 19
gagtcgacgg tagtctgctt cagcctggta atgcctgacg gcgctcggcg atctccgacc      60

<210> SEQ ID NO 20
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 20

<400> SEQUENCE: 20
gatcggtgct catgtgtatg gacgctacgg gaccgcagta cggcacgttg ctatcgctta     60
tgtctcgaat c                                                          71

<210> SEQ ID NO 21
<211> LENGTH: 55
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 21

<400> SEQUENCE: 21
gacggtagtc tgcttcagcc tggtaatgcc tgacggcgct cggcgatctc cgaag           55

<210> SEQ ID NO 22
<211> LENGTH: 68
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 22

<400> SEQUENCE: 22
gacacgcatc agtgtcacga acgactgcgt acacggacag cgcaggactg tctagctcca      60
gtgggatc                                                              68

<210> SEQ ID NO 23
<211> LENGTH: 55
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 23

<400> SEQUENCE: 23
gacggtagtc tgcttcagcc tggtaatgcc tgacggcgct cggcgatctc gaatg            55

<210> SEQ ID NO 24
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 24

<400> SEQUENCE: 24
agcgcattac tgcccacgta gtcttcgata acctgtaagt atcgcgtggt cggtactttt       60
gtacctacac cgcgatccag a                                                 81

<210> SEQ ID NO 25
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 25

<400> SEQUENCE: 25
gtcgtgcagt atggtatttt taccagtcag gacgaccgtg cgacgccctc acatctggca       60
acgagtgtac g                                                            71

<210> SEQ ID NO 26
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 26

<400> SEQUENCE: 26
cgtggcctga catgcgctcg aacactgact gat                                    33

<210> SEQ ID NO 27
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 27

<400> SEQUENCE: 27
atcactatga cgattcggac catcgttgac tta                                    33

<210> SEQ ID NO 28
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 28

<400> SEQUENCE: 28
caggttggcg tagactaatc agcac                                              25

<210> SEQ ID NO 29
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 29

<400> SEQUENCE: 29
gctaactgtg tgagatcgac gcacg                                              25

<210> SEQ ID NO 30
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 30

<400> SEQUENCE: 30
caggttatcg aagactagca tgagc                                              25

<210> SEQ ID NO 31
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 31

<400> SEQUENCE: 31
agccgtactg tgagggcgtc gcacg                                              25

<210> SEQ ID NO 32
<211> LENGTH: 77
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 32

<400> SEQUENCE: 32
tattactgcc cacggacggc tcgattacct gtaagtgtcg cgtggtcggt actttgtac         60 ctacaccgcg acttcga                                                       77

<210> SEQ ID NO 33
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 33

<400> SEQUENCE: 33
gtcgtgcagt atggtatttt taccacacag aacgaccgtg cgctgccact acatcgaaca    60
acgagtgtac g                                                         71

<210> SEQ ID NO 34
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 34

<400> SEQUENCE: 34
cgtggtctgt gataacttgc attgagcga                                      29

<210> SEQ ID NO 35
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 35

<400> SEQUENCE: 35
atctgcgtgt cagttcggac catcgttgac tta                                 33

<210> SEQ ID NO 36
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 36

<400> SEQUENCE: 36
caggtaggca ggccgtcgcc agact                                          25

<210> SEQ ID NO 37
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 37

<400> SEQUENCE: 37
tcgtagcttg tagtatcgac gcacg                                          25

<210> SEQ ID NO 38
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 38

<400> SEQUENCE: 38

```
caggtaatcg agccgtcggt actgg                                          25
```

<210> SEQ ID NO 39
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 39

<400> SEQUENCE: 39

```
ggccaagttg tagtggcagc gcacg                                          25
```

<210> SEQ ID NO 40
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 40

<400> SEQUENCE: 40

```
gtagtcgatg taccaccatg cagtcttttg actgcatgga cagcgcagga cgatcagcca    60
agctacggtc g                                                         71
```

<210> SEQ ID NO 41
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 41

<400> SEQUENCE: 41

```
ctacacctgc gctgtggcgt                                                20
```

<210> SEQ ID NO 42
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 42

<400> SEQUENCE: 42

```
gtagcttggc tgatcgtggg cctatacgca cgtactgacg gctatcacgc ggtatgccat    60
catg                                                                 64
```

<210> SEQ ID NO 43
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 43
<220> FEATURE:
<221> NAME/KEY: misc_feature
<222> LOCATION: (1)..(1)

```
<223> OTHER INFORMATION: Nucleotide 1 is modified with a phosphate
      group.

<400> SEQUENCE: 43
catgatggca taccgcgtga tagccgtcag tacgtgcgta taggccctgt agacgcctgg    60
tacatcgact ac                                                       72

<210> SEQ ID NO 44
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 44

<400> SEQUENCE: 44
gcacgaacag tagatgcgct aagcagattg cacacatagt tgcgtcaccg atcatccagt    60
cgtc                                                                64

<210> SEQ ID NO 45
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 45

<400> SEQUENCE: 45
gactcgacga ctggatgatc ggacagccgt ctagctggcc gcttgtcgcg ttaccgtatg    60
caggacgtac atcgcaccac tgccta                                        86

<210> SEQ ID NO 46
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 46

<400> SEQUENCE: 46
agcggccagc tagacggctg tggcgtagcc atgctatcac gctgatggtc ggcattgact    60
acacctgcat acggtaacgc gaca                                          84

<210> SEQ ID NO 47
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 47

<400> SEQUENCE: 47
agtggtgcga tgtacgtggg cactcattac ttggcaaggt actaggtcca ttcgctcagt    60
tatc                                                                64

<210> SEQ ID NO 48
```

<211> LENGTH: 136
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 48
<220> FEATURE:
<221> NAME/KEY: misc_feature
<222> LOCATION: (1)..(1)
<223> OTHER INFORMATION: Nucleotide 1 is modified with a phosphate
      group.

<400> SEQUENCE: 48
gataactgag cgaatggacc tagtaccttg ccaagtaatg agtgccctgt agtcaatgcc    60
gaccatcagc gtgatagcat ggctacgcct gacgcaacta tgtgtgcaat ctgcttagcg   120
catctactgt tcgtgc                                                   136

<210> SEQ ID NO 49
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 49

<400> SEQUENCE: 49
gcacgaacag tagatgcgcg gagcagtgat ggtcggcatt gactacaccg atcatccagt    60
cgtc                                                                64

<210> SEQ ID NO 50
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 50

<400> SEQUENCE: 50
gactcgacga ctggatgatc ggacagccgt ctagctggcc tattgtcgcg ttaccgtatg    60
caggacgtac atcgccggat taagcg                                        86

<210> SEQ ID NO 51
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 51

<400> SEQUENCE: 51
ataggccagc tagacggctg tgggcactca ttacttggca agattgcaca catagttgcg    60
tcacctgcat acggtaacgc gaca                                          84

<210> SEQ ID NO 52
<211> LENGTH: 64
<212> TYPE: DNA
<213> ORGANISM: Artificial
<220> FEATURE:

```
<223> OTHER INFORMATION: Synthetic
<220> FEATURE:
<221> NAME/KEY: misc_feature
<223> OTHER INFORMATION: Strand 52

<400> SEQUENCE: 52
aatccggcga tgtacgtggc gtagccatgc tatcgttggt actaggtcca ttcgctcagt    60
tatc                                                                 64

<210> SEQ ID NO 53
<211> LENGTH: 136
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 53
<220> FEATURE:
<221> NAME/KEY: misc_feature
<222> LOCATION: (1)..(1)
<223> OTHER INFORMATION: Nucleotide 1 is modified with a phosphate
      group.

<400> SEQUENCE: 53
gataactgag cgaatggacc tagtaccaac gatagcatgg ctacgcctga cgcaactatg    60
tgtgcaatct tgccaagtaa tgagtgccct gtagtcaatg ccgaccatca ctgctccgcg   120
catctactgt tcgtgc                                                   136

<210> SEQ ID NO 54
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 54

<400> SEQUENCE: 54
gcacgaacag tagatgcgcg gagcagtgat aagcggcaga cactacaccg atcatccagt    60
caac                                                                 64

<210> SEQ ID NO 55
<211> LENGTH: 99
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 55

<400> SEQUENCE: 55
tgttagcgcc tgacgcaact atgtgtgcaa tcttgccaag taattggtgc cctgtagtgt    60
ctgccgctta tcactgctcc gcgcatctac tgttcgtgc                           99

<210> SEQ ID NO 56
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 56
```

```
<400> SEQUENCE: 56
tggtcgttga ctggatgatc ggacagccgt ctagctggcc tattgtcgcg ttaccgtatg    60
caggacgtac atcgccggat tcattc                                        86

<210> SEQ ID NO 57
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 57

<400> SEQUENCE: 57
ataggccagc tagacggctg tgggcaccaa ttacttggca agattgcaca catagttgcg    60
tcacctgcat acggtaacgc gaca                                          84

<210> SEQ ID NO 58
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 58

<400> SEQUENCE: 58
aatccggcga tgtacgtggc gctaaca                                       27

<210> SEQ ID NO 59
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 59

<400> SEQUENCE: 59
gcacgaacag tagatgcgct aagcagattg cacacatagt tgcgtcaccg atcatccgtt    60
gaac                                                                64

<210> SEQ ID NO 60
<211> LENGTH: 99
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 60

<400> SEQUENCE: 60
atgagtgccc tgtagtcaat gccgagcctc agcgtgatag catggctacg cctgacgcaa    60
ctatgtgtgc aatctgctta gcgcatctac tgttcgtgc                          99

<210> SEQ ID NO 61
<211> LENGTH: 86
<212> TYPE: DNA
<213> ORGANISM: Artificial
<220> FEATURE:
```

<223> OTHER INFORMATION: Synthetic
<220> FEATURE:
<221> NAME/KEY: misc_feature
<223> OTHER INFORMATION: Strand 61

<400> SEQUENCE: 61
tggtcgttca acggatgatc ggacagccgt ctagctggcc gcttgtcgcg ttaccgtatg    60
caggacgtac atcgcaccag acttcg                                        86

<210> SEQ ID NO 62
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 62

<400> SEQUENCE: 62
agcggccagc tagacggctg tggcgtagcc atgctatcac gctgaggctc ggcattgact    60
acacctgcat acggtaacgc gaca                                          84

<210> SEQ ID NO 63
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 63

<400> SEQUENCE: 63
tctggtgcga tgtacgtggg cactcat                                       27

<210> SEQ ID NO 64
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 64

<400> SEQUENCE: 64
gcacacatga gcacgatatt agcgcagcgt gagtcatagt tgcgtcaccg atcatcagca    60
tcca                                                                64

<210> SEQ ID NO 65
<211> LENGTH: 99
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 65

<400> SEQUENCE: 65
gaatcgaccc tgtagtgcaa tctactgcta tacttgaccg catggctacg cctgacgcaa    60
ctatgactca cgctgcgcta atatcgtgct catgtgtgc                          99

<210> SEQ ID NO 66

```
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 66

<400> SEQUENCE: 66
tggactggat gctgatgatc ggacagccgt ctagctggcc gcttgtcgcg ttaccgtatg    60
caggacgtac atcgcaccag acattc                                        86

<210> SEQ ID NO 67
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 67

<400> SEQUENCE: 67
agcggccagc tagacggctg tggcgtagcc atgcggtcaa gtatagcagt agattgcact    60
acacctgcat acggtaacgc gaca                                          84

<210> SEQ ID NO 68
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 68

<400> SEQUENCE: 68
tctggtgcga tgtacgtggg tcgattc                                       27

<210> SEQ ID NO 69
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 69

<400> SEQUENCE: 69
gcacaatgcg ggtggataat gtgagtgata tgaccatagt tgcgtcaccg atcatccggc    60
atca                                                                64

<210> SEQ ID NO 70
<211> LENGTH: 99
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 70

<400> SEQUENCE: 70
gagcgtgccc tgtagtacca ctgccaacag aggtcgatag catggctacg cctgacgcaa    60
```
ctatggtcat atcactcaca ttatccaccc gcattgtgc          99

<210> SEQ ID NO 71
<211> LENGTH: 86
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 71

<400> SEQUENCE: 71
tggactgatg ccggatgatc ggacagccgt ctagctggcc gcttgtcgcg ttaccgtatg    60
caggacgtac atcgcaccag acttcg                                        86

<210> SEQ ID NO 72
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 72

<400> SEQUENCE: 72
agcggccagc tagacggctg tggcgtagcc atgctatcga cctctgttgg cagtggtact    60
acacctgcat acggtaacgc gaca                                          84

<210> SEQ ID NO 73
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 73

<400> SEQUENCE: 73
tctggtgcga tgtacgtggg cacgctc                                       27

<210> SEQ ID NO 74
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 74
<220> FEATURE:
<221> NAME/KEY: misc_feature
<222> LOCATION: (46)..(46)
<223> OTHER INFORMATION: Nucleotide 46 is modified with biotin.
<220> FEATURE:
<221> NAME/KEY: misc_feature
<222> LOCATION: (49)..(49)
<223> OTHER INFORMATION: Nucleotide 49 is modified with biotin.

<400> SEQUENCE: 74
cgactcacgt actgcactac gatcacccgg gatcgcaccg tcttttttg acggtgcgat     60 cccgggtgat cgtagt                                                   76

<210> SEQ ID NO 75
<211> LENGTH: 84

```
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 75

<400> SEQUENCE: 75
cgctaatcat gttaccagct atctacatcg accgctcagc ctgtgtgatg ctgtcagtca      60
ccatacgctg ctagtccact gtac                                            84

<210> SEQ ID NO 76
<211> LENGTH: 82
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 76

<400> SEQUENCE: 76
gcagtacgtg agtcggtaca gtggactagc agcgtatggt gtgacagcat cacacaggct      60
gagcggtcga tgtagatagc tg                                              82

<210> SEQ ID NO 77
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (31)..(31)
<223> OTHER INFORMATION: Strand 77
<220> FEATURE:
<221> NAME/KEY: misc_feature
<222> LOCATION: (31)..(31)
<223> OTHER INFORMATION: Nucleotide 31 is modified with biotin.
<220> FEATURE:
<221> NAME/KEY: misc_feature
<222> LOCATION: (34)..(34)
<223> OTHER INFORMATION: Nucleotide 34 is modified with biotin.

<400> SEQUENCE: 77
acgttggatt gggccctgat cgtagtgttt ttttcactac gatcagggcc caatccaacg      60
tcgctaatca tgttac                                                     76

<210> SEQ ID NO 78
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 78

<400> SEQUENCE: 78
gtacagtgga ctagcagcgt atggtgactg acagcatcac acaggctgag cggtcgatgt      60
agatagctgg taacatgatt agcg                                            84

<210> SEQ ID NO 79
<211> LENGTH: 84
<212> TYPE: DNA
<213> ORGANISM: Artificial
```

```
<220> FEATURE:
<223> OTHER INFORMATION: Synthetic
<220> FEATURE:
<221> NAME/KEY: misc_feature
<223> OTHER INFORMATION: Strand 79

<400> SEQUENCE: 79
cagctatcta catcgaccgc tcagcctgtg tgatgctgtc agtcaccata cgctgctagt      60
ccactgtacg attcgagaca taag                                            84

<210> SEQ ID NO 80
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 28
<220> FEATURE:
<221> NAME/KEY: misc_feature
<222> LOCATION: (1)..(1)
<223> OTHER INFORMATION: Nucleotide 1 is modified with biotin.

<400> SEQUENCE: 80
gtgctgatta gtctacgcca acctg                                           25

<210> SEQ ID NO 81
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 29
<220> FEATURE:
<221> NAME/KEY: misc_feature
<222> LOCATION: (1)..(1)
<223> OTHER INFORMATION: Nucleotide 1 is modified with biotin.

<400> SEQUENCE: 81
cgtgcgtcga tctcacacag ttagc                                           25

<210> SEQ ID NO 82
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 30
<220> FEATURE:
<221> NAME/KEY: misc_feature
<222> LOCATION: (1)..(1)
<223> OTHER INFORMATION: Nucleotide 1 is modified with biotin.

<400> SEQUENCE: 82
gctcatgcta gtcttcgata acctg                                           25

<210> SEQ ID NO 83
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 31
```

```
<220> FEATURE:
<221> NAME/KEY: misc_feature
<222> LOCATION: (1)..(1)
<223> OTHER INFORMATION: Nucleotide 1 is modified with biotin.

<400> SEQUENCE: 83
cgtgcgacgc cctcacagta cggct                                              25

<210> SEQ ID NO 84
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 36
<220> FEATURE:
<221> NAME/KEY: misc_feature
<222> LOCATION: (1)..(1)
<223> OTHER INFORMATION: Nucleotide 1 is modified with biotin.

<400> SEQUENCE: 84
agtctggcga cggcctgcct acctg                                              25

<210> SEQ ID NO 85
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 37
<220> FEATURE:
<221> NAME/KEY: misc_feature
<222> LOCATION: (1)..(1)
<223> OTHER INFORMATION: Nucleotide 1 is modified with biotin.

<400> SEQUENCE: 85
cgtgcgtcga tactacaagc tacga                                              25

<210> SEQ ID NO 86
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 38
<220> FEATURE:
<221> NAME/KEY: misc_feature
<222> LOCATION: (1)..(1)
<223> OTHER INFORMATION: Nucleotide 1 is modified with biotin.

<400> SEQUENCE: 86
ccagtaccga cggctcgatt acctg                                              25

<210> SEQ ID NO 87
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Fuel strand for strand 39
<220> FEATURE:
<221> NAME/KEY: misc_feature
<222> LOCATION: (1)..(1)
```

<223> OTHER INFORMATION: Nucleotide 1 is modified with biotin.

<400> SEQUENCE: 87
cgtgcgctgc cactacaact tggcc                                          25

<210> SEQ ID NO 88
<211> LENGTH: 307
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: PX1-PX2 ligation product

<400> SEQUENCE: 88
tgttagcgcc tgacgcaact atgtgtgcaa tcttgccaag taattggtgc cctgtagtgt     60
ctgccgctta tcactgctcc gcgcatctac tgttcgtgcg ataactgagc gaatggacct    120
agtaccttgc caagtaatga gtgccctgta gtcaatgccg accatcagcg tgatagcatg    180
gctacgcctg acgcaactat gtgtgcaatc tgcttagcgc atctactgtt cgtgccatga    240
tggcataccg cgtgatagcc gtcagtacgt gcgtataggc cctgtagacg cctggtacat    300
cgactac                                                             307

<210> SEQ ID NO 89
<211> LENGTH: 307
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: PX1-JX22 ligation product

<400> SEQUENCE: 89
atgagtgccc tgtagtcaat gccgagcctc agcgtgatag catggctacg cctgacgcaa     60
ctatgtgtgc aatctgctta gcgcatctac tgttcgtgcg ataactgagc gaatggacct    120
agtaccttgc caagtaatga gtgccctgta gtcaatgccg accatcagcg tgatagcatg    180
gctacgcctg acgcaactat gtgtgcaatc tgcttagcgc atctactgtt cgtgccatga    240
tggcataccg cgtgatagcc gtcagtacgt gcgtataggc cctgtagacg cctggtacat    300
cgactac                                                             307

<210> SEQ ID NO 90
<211> LENGTH: 307
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: JX21-PX2 ligation product

<400> SEQUENCE: 90
gagcgtgccc tgtagtacca ctgccaacag aggtcgatag catggctacg cctgacgcaa     60
ctatggtcat atcactcaca ttatccaccc gcattgtgcg ataactgagc gaatggacct    120
agtaccaacg atagcatggc tacgcctgac gcaactatgt gtgcaatctt gccaagtaat    180
gagtgccctg tagtcaatgc cgaccatcac tgctccgcgc atctactgtt cgtgccatga    240
tggcataccg cgtgatagcc gtcagtacgt gcgtataggc cctgtagacg cctggtacat    300 cgactac					307

<210> SEQ ID NO 91
<211> LENGTH: 307
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: JX21-JX22 ligation product

<400> SEQUENCE: 91
gaatcgaccc tgtagtgcaa tctactgcta tacttgaccg catggctacg cctgacgcaa     60
ctatgactca cgctgcgcta atatcgtgct catgtgtgcg ataactgagc gaatggacct    120
agtaccaacg atagcatggc tacgcctgac gcaactatgt gtgcaatctt gccaagtaat    180
gagtgccctg tagtcaatgc cgaccatcac tgctccgcgc atctactgtt cgtgccatga    240
tggcataccg cgtgatagcc gtcagtacgt gcgtataggc cctgtagacg cctggtacat    300 cgactac					307

<210> SEQ ID NO 92
<211> LENGTH: 37
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: COVER-JX-1

<400> SEQUENCE: 92
acacugcgcu acgguuguga guacguucgc cuagccg					37

<210> SEQ ID NO 93
<211> LENGTH: 37
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: COVER-PX-1

<400> SEQUENCE: 93
gagcgucgca agggucgagu ggacgacugg ucaggua					37

<210> SEQ ID NO 94
<211> LENGTH: 37
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: COVER-JX-2

<400> SEQUENCE: 94
cagcuucgau aagcgcgagu gguaggucug agugaga					37

<210> SEQ ID NO 95
<211> LENGTH: 37
<212> TYPE: RNA
<213> ORGANISM: Artificial
<220> FEATURE:
<223> OTHER INFORMATION: Synthetic -continued

```
<220> FEATURE:
<221> NAME/KEY: misc_feature
<223> OTHER INFORMATION: COVER-PX-2

<400> SEQUENCE: 95
auuacaguuc cggcguguga guuagacucc uaugcag                              37

<210> SEQ ID NO 96
<211> LENGTH: 37
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: ANTI-COVER-JX-1
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 96
cggctaggcg aacgtactca caaccgtagc gcagtgt                              37

<210> SEQ ID NO 97
<211> LENGTH: 37
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: ANTI-COVER-PX-1
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 97
tacctgacca gtcgtccact cgaccctgc gacgctc                               37

<210> SEQ ID NO 98
<211> LENGTH: 37
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: ANTI-COVER-JX-2
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 98
tctcactcag acctaccact cgcgcttatc gaagctg                              37

<210> SEQ ID NO 99
<211> LENGTH: 37
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: ANTI-COVER-PX-2
<220> FEATURE:
```

```
<221> NAME/KEY: misc_feature
<222> LOCATION: (1)..(1)
<223> OTHER INFORMATION: Nucleotide at position 1 is modified with a
      Biotin group.

<400> SEQUENCE: 99
ctgcatagga gtctaactca cacgccggaa ctgtaat                              37

<210> SEQ ID NO 100
<211> LENGTH: 54
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: SET-1

<400> SEQUENCE: 100
gtcgtactca caaccgtagc gcagtgttac ctgaccagtc gtccactcga ccgt           54

<210> SEQ ID NO 101
<211> LENGTH: 54
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: SET-2

<400> SEQUENCE: 101
acctaactca cacgccggaa ctgtaattct cactcagacc taccactcgc gccg           54

<210> SEQ ID NO 102
<211> LENGTH: 101
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: LH-1

<400> SEQUENCE: 102
tgccaagcct ccagccacct tttggtggct ggaggaccga tgcggcgcga gtggtaggtg     60
ccgagcacac ctcatgcctt ttggcatgag gtgtatccgc t                        101

<210> SEQ ID NO 103
<211> LENGTH: 101
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: LH-2

<400> SEQUENCE: 103
catcggttca ccgcacgtct tttgacgtgc ggtgacttgg caacggttgt gagtacgaca     60
gcggatcgtc cgaatcactt ttgtgattcg gcaggctcgg c                        101

<210> SEQ ID NO 104
<211> LENGTH: 36
<212> TYPE: RNA
<213> ORGANISM: Artificial
<220> FEATURE:
```

```
<223> OTHER INFORMATION: Synthetic
<220> FEATURE:
<221> NAME/KEY: misc_feature
<223> OTHER INFORMATION: CJX-1D-1

<400> SEQUENCE: 104
agauuccacg agcuccucag ccgaaccuca ucugga                            36

<210> SEQ ID NO 105
<211> LENGTH: 36
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: CPX-1D-1

<400> SEQUENCE: 105
cacagcaucg uagccagucc ucaugcgugg cuuacc                            36

<210> SEQ ID NO 106
<211> LENGTH: 36
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: CJX-1D-2

<400> SEQUENCE: 106
cugacagucg augccagguu gguugcguag uucacc                            36

<210> SEQ ID NO 107
<211> LENGTH: 36
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: CPX-1D-2

<400> SEQUENCE: 107
agaccuaccg agcguuggug ccgaugucaa gcaguc                            36

<210> SEQ ID NO 108
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Anti-CJX-1D-1
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 108
tccagatgag gttcggctga ggagctcgtg gaatct                            36

<210> SEQ ID NO 109
<211> LENGTH: 36
<212> TYPE: DNA
<213> ORGANISM: Artificial
```

-continued

```
<220> FEATURE:
<223> OTHER INFORMATION: Synthetic
<220> FEATURE:
<221> NAME/KEY: misc_feature
<223> OTHER INFORMATION: Anti-CPX-1D-1
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 109
ggtaagccac gcatgaggac tggctacgat gctgtg                                    36

<210> SEQ ID NO 110
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Anti-CJX-1D-2
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 110
ggtgaactac gcaaccaacc tggcatcgac tgtcag                                    36

<210> SEQ ID NO 111
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Anti-CPX-1D-2
<220> FEATURE:
<221> NAME/KEY: misc_feature
<222> LOCATION: (1)..(1)
<223> OTHER INFORMATION: Nucleotide at position 1 is modified with a
      Biotin group.

<400> SEQUENCE: 111
gactgcttga catcggcacc aacgctcggt aggtct                                    36

<210> SEQ ID NO 112
<211> LENGTH: 48
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Set-1D-1

<400> SEQUENCE: 112
tcggctgagg agctcgtgga atctggtaag ccacgcatga ggactggc                       48

<210> SEQ ID NO 113
<211> LENGTH: 48
<212> TYPE: DNA
<213> ORGANISM: Artificial
```

```
<220> FEATURE:
<223> OTHER INFORMATION: Synthetic
<220> FEATURE:
<221> NAME/KEY: misc_feature
<223> OTHER INFORMATION: Set-1D-2

<400> SEQUENCE: 113
tcggcaccaa cgctcggtag gtctggtgaa ctacgcaacc aacctggc                    48

<210> SEQ ID NO 114
<211> LENGTH: 23
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-1

<400> SEQUENCE: 114
ggcagcttat cgtcggaagc ggc                                               23

<210> SEQ ID NO 115
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-3

<400> SEQUENCE: 115
tcgatgacga cacctcc                                                      17

<210> SEQ ID NO 116
<211> LENGTH: 125
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-4

<400> SEQUENCE: 116
gctcgaagga ttcgtagtcg ttggcgtcga gctcctcagc cgagccgctc gtgtcgataa       60
ctgttcatag ccgtcttagg agagtcagaa tggcaaggtg gcggagagct tttttatcac      120
ttacc                                                                  125

<210> SEQ ID NO 117
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-5

<400> SEQUENCE: 117
acgccactga gtacgaatcc ttcgagcgac gcagccgt                               38
```

```
<210> SEQ ID NO 118
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-7

<400> SEQUENCE: 118
gcgaagtaga tgcggacaac gctggacctt gccattctga ctctcctaag acggctatga      60
acagcacgga acacggtcgg t                                                81

<210> SEQ ID NO 119
<211> LENGTH: 56
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-8

<400> SEQUENCE: 119
ggaggtctca gcatggagcc aggttggttg ggtaccgact ccgatccgtg cctgcc          56

<210> SEQ ID NO 120
<211> LENGTH: 124
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-9

<400> SEQUENCE: 120
gctccaagcg aggagtgtga ttttttctga cgatgtggct ctggagtttt ttcaggtgct      60
gtggctcaag gttttttttac gcacttctcc accgagtagg ctggcatctt ttttagagac    120
aacc                                                                  124

<210> SEQ ID NO 121
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-10

<400> SEQUENCE: 121
tatccaagtg agtcgtgatc tttttggac caggcacctc gtggcatttt ttatctgccg       60
ac                                                                    62

<210> SEQ ID NO 122
<211> LENGTH: 88
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-11
```

<400> SEQUENCE: 122
tgagcgtgga gtggaacgac tttttttgatc cgtacaccat cggtgatttt ttactccgag    60
caccgcatct acttcgcacg gctgcgtc                                       88

<210> SEQ ID NO 123
<211> LENGTH: 90
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-12

<400> SEQUENCE: 123
ggtggagaag tgcgtacctt gagcctcaca gctcctgcct ggtccgatca cgactcactt    60
ggataggttg tctctgatgc cagcctactc                                     90

<210> SEQ ID NO 124
<211> LENGTH: 90
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-13

<400> SEQUENCE: 124
tccacgctca gtcggcagat tgccacgagg acatcggcgg acagcacctg ctccagagcc    60
tcagcacgcc tgtacggatc gtcgttccac                                     90

<210> SEQ ID NO 125
<211> LENGTH: 90
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-14

<400> SEQUENCE: 125
cgcttggagc ggtaagtgta gctctccgcc tctgcctacc tgctcggagt tcaccgatgg    60
actctggtgg acatcgtcag tcacactcct                                     90

<210> SEQ ID NO 126
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-15

<400> SEQUENCE: 126
gttgtggtag gcagaccagc                                                20

<210> SEQ ID NO 127
<211> LENGTH: 20
<212> TYPE: DNA
<213> ORGANISM: Artificial
<220> FEATURE:

```
<223> OTHER INFORMATION: Synthetic
<220> FEATURE:
<221> NAME/KEY: misc_feature
<223> OTHER INFORMATION: Strand-1d-16

<400> SEQUENCE: 127
agagtggcgt gctgaccacc                                              20

<210> SEQ ID NO 128
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand-1d-17

<400> SEQUENCE: 128
gatgtggagc tgtgaccgcc                                              20
```